US012416053B2

(12) United States Patent
Kundu et al.

(10) Patent No.: US 12,416,053 B2
(45) Date of Patent: Sep. 16, 2025

(54) PRIMER SETS, BIOMARKERS, KIT AND APPLICATIONS THEREOF

(71) Applicant: Indian Institute of Technology Delhi, New Delhi (IN)

(72) Inventors: Bishwajit Kundu, New Delhi (IN); Akhilesh Mishra, New Delhi (IN); Parul Gupta, New Delhi (IN); Ashutosh Kumar Pandey, New Delhi (IN); Prashant Pradhan, New Delhi (IN); Manoj B. Menon, New Delhi (IN); James Gomes, New Delhi (IN); Vivekanandan Perumal, New Delhi (IN); Sonam Dhamija, New Delhi (IN)

(73) Assignee: INDIAN INSTITUTE OF TECHNOLOGY DELHI

( * ) Notice: Subject to any disclaimer, the term of this patent is extended or adjusted under 35 U.S.C. 154(b) by 1046 days.

(21) Appl. No.: 17/422,575

(22) PCT Filed: Jun. 3, 2020

(86) PCT No.: PCT/IN2020/050495
§ 371 (c)(1),
(2) Date: Jul. 13, 2021

(87) PCT Pub. No.: WO2021/156882
PCT Pub. Date: Aug. 12, 2021

(65) Prior Publication Data
US 2022/0002824 A1 Jan. 6, 2022

(30) Foreign Application Priority Data

Feb. 4, 2020 (IN) .............................. 202011004922
Apr. 27, 2020 (IN) .............................. 202011018018

(51) Int. Cl.
*C12Q 1/70* (2006.01)
*C07K 14/005* (2006.01)

(52) U.S. Cl.
CPC ............ *C12Q 1/701* (2013.01); *C07K 14/005* (2013.01); *C12Q 2600/158* (2013.01)

(58) Field of Classification Search
CPC . C12Q 1/701; C12Q 2600/158; C07K 14/005
See application file for complete search history.

(56) References Cited

PUBLICATIONS

Wu F, Zhao S, Yu B, Chen YM, Wang W, Song ZG, Hu Y, Tao ZW, Tian JH, Pei YY, Yuan ML, Zhang YL, Dai FH, Liu Y, Wang QM , Zheng JJ, Xu L, Holmes EC, Zhang YZ. A new coronavirus associated with human respiratory disease in China. Nature. Mar. 2020;579(7798):265-269. (Year: 2020).*

Corman et al. Detection of 2019 novel coronavirus (2019-nCOV) by real-time RT-PCR. Euro Surveill. Jan. 2020;25(3):2000045. (Year: 2020).*
Zhou et al. A pneumonia outbreak associated with a new coronavirus of probable bat origin. Nature. Mar. 2020;579(7798):270-273. (Year: 2020).*
China CDC Primers and Probes for detection 2019-nCOV: (https://www.who.int/docs/default-source/coronaviruse/whoinhouseassays.pdf, posted on Jan. 24, 2020. (Year: 2020).*
SYBR Green qPCR Supermixes. Bio-Rad ( https://www.bio-rad.com/en-us/feature/sybr-green-for-qpcr.html)—Aug. 12, 2024 (Year: 2024).*
De la Torre D, Astolfi-Ferreira CS, Chacon RD, Piantino Ferreira AJ. Sensitive SYBR Green-Real Time PCR for the Detection and Quantitation of Avian Rotavirus A. Vet Sci. Dec. 29, 2018;6(1):2. (Year: 2018).*
Tajadini M, Panjehpour M, Javanmard SH. Comparison of SYBR Green and TaqMan methods in quantitative real-time polymerase chain reaction analysis of four adenosine receptor subtypes. Adv Biomed Res. Feb. 28, 2014;3:85.( (Year: 2014).*
Corman et al., "Detection of 2019 novel coronavirus (2019-nCOV) by real-time RT-PCR," Eurosurveillance, vol. 25, No. 3, pp. 23-30 (2020).
Deng et al., "Analysis of Coronavirus Temperature-Sensitive Mutants Reveals an Interplay between the Macrodomain and Papain-Like Protease Impacting Replication and Pathogenesis," Journal of Virology, vol. 93, No. 12:e02140-18, pp. 1-16 (2019).
Habibzadeh et al., "Molecular diagnostic assays for COVID-19: an overview," Critical Reviews in Clinical Laboratory Sciences, pp. 1-14 (2021).
Summary table of available protocols in this document, National Institute of Health, 80 pages (2020).
Wu et al., "A new coronavirus associated with human respiratory disease in China," Nature, vol. 579, starting at p. 265 (20 pages) (2020).
Zhou et al., "A pneumonia outbreak associated with a new coronavirus of probable bat origin," Nature, vol. 579, starting at p. 270 (20 pages) (2020).
Schmittgen et al., "Quantitative Reverse Transcription-Polymerase Chain Reaction to Study mRNA Decay: Comparison of Endpoint and Real-Time Methods," Analytical Biochemistry, vol. 285, pp. 194-204 (2000).

* cited by examiner

*Primary Examiner* — Janet L Andres
*Assistant Examiner* — Ruixue Wang
(74) *Attorney, Agent, or Firm* — Panitch Scwharze Belisario & Nadel LLP

(57) ABSTRACT

A method of detecting the presence of SARS-CoV-2 using oligonucleotide primer pairs is disclosed. Oligonucleotide primer pairs for the detection of SARS-CoV-2 using polymerase chain reaction (PCR)-based methods are also disclosed. Further, biomarkers and probes for SARS-CoV-2 detection are disclosed. The disclosure also relates to the identification and isolation of biomarkers for use as probes for the detection of SARS-CoV-2 and further use of the biomarkers as a target for the development of drug targets and therapeutics for SARS-CoV-2.

18 Claims, 9 Drawing Sheets

Specification includes a Sequence Listing.

PRIMER SETS, BIOMARKERS, KIT AND APPLICATIONS THEREOF

CROSS-REFERENCE TO RELATED APPLICATIONS

This application is a Section 371 of International Application No. PCT/IN2020/050495, filed Jun. 3, 2020, which has not yet published, and which claims priority under 35 U.S.C. § 119 (b) to Indian Application No. 202011004922, filed Feb. 4, 2020, and Indian Application No. 202011018018, filed Apr. 27, 2020, the disclosures of which are incorporated herein by reference in their entirety.

REFERENCE TO SEQUENCE LISTING SUBMITTED ELECTRONICALLY

This application contains a sequence listing, which is submitted electronically via EFS-Web as an ASCII formatted sequence listing with a file name "689370_10US_Sequence Listing", creation date of Mar. 4, 2021, and having a size of about 8 KB. The sequence listing submitted via EFS-Web is part of the specification and is herein incorporated by reference in its entirety.

FIELD OF INVENTION

The present disclosure broadly relates to a process for detecting the presence of SARS-CoV-2, particularly, it relates to primers for detection of the SARS-CoV-2 and its method of detection thereof. The disclosure also relates to the identification and isolation of biomarkers for use as probes for the detection of SARS-CoV-2 and further use of biomarkers for the development of drug targets and therapeutics for the treatment of SARS-CoV-2 infection.

BACKGROUND OF THE INVENTION

The threat to the world population caused by viruses is a problem that remains to be addressed. One of the major drawbacks in providing a therapeutic intervention to the infections caused by viruses is the timely detection of the type of virus causing the infection. Therefore, a knowledge gap still exists in providing effective assays for the detection and treatment of infections caused by a life-threatening or contagious virus.

The globe is currently witnessing a major pandemic caused by a new strain of coronavirus (named as COVID-19). The origin and evolution of COVID-19 remain elusive. The infection is highly contagious, and early detection and therapy can help the infected person to survive. Needless to mention that in several cases, the virus infection is asymptomatic and can remain in an incubation period for a long time. Therefore, early detection becomes necessary to trace the viral infection and start timely treatment and medication. Early detection of COVID-19 in the population is required as people who carry the SARS-CoV-2 can be kept in isolation or quarantine to protect others from getting infected with the SARS-CoV-2.

SUMMARY OF INVENTION

In a first aspect of the present disclosure, there is provided a process for detecting the presence of SARS-CoV-2 in a sample, said process comprising: (a) isolating RNA from a sample; (b) preparing DNA from RNA by reverse transcriptase reaction and performing nucleic acid amplification reaction employing an oligonucleotide primer pair to produce an amplicon, wherein the set of primer pairs is selected from the group consisting of a nucleic acid sequence as set forth in SEQ ID NO: 6 and SEQ ID NO: 7, SEQ ID NO: 8 and SEQ ID NO: 9, SEQ ID NO: 6 and SEQ ID NO: 9, SEQ ID NO: 10 and SEQ ID NO: 11, SEQ ID NO: 12 and SEQ ID NO: 13, SEQ ID NO: 14 and SEQ ID NO: 15, SEQ ID NO: 16 and SEQ ID NO: 17, SEQ ID NO: 6 and SEQ ID NO: 13, SEQ ID NO: 6 and SEQ ID NO: 11, SEQ ID NO: 8 and SEQ ID NO: 11, SEQ ID NO: 8 and SEQ ID NO: 13, SEQ ID NO: 10 and SEQ ID NO: 13, and SEQ ID NO: 12 and SEQ ID NO: 11; and (c) detecting the presence or absence of the amplicon, wherein the presence of the amplicon indicates the presence of SARS-CoV-2 in the sample.

In a second aspect of the present disclosure, there is provided a process for detecting the presence of SARS-CoV-2 in a sample, said process comprising: (a) preparing nucleic acid from a sample; (b) performing nucleic acid amplification reaction employing the nucleic acid of step (a) and one or more oligonucleotide primer pairs for producing one or more amplicons, wherein the amplicon comprises a nucleic acid sequence selected from the group consisting of SEQ ID NO: 1, SEQ ID NO: 2, SEQ ID NO: 3, SEQ ID NO: 4, and SEQ ID NO: 5; and (c) detecting the presence or absence of one or more amplicons, wherein the presence of one or more amplicons indicates the presence of SARS-CoV-2 in the sample.

In a third aspect of the present disclosure, there is provided a process for detecting the presence of SARS-CoV-2 in a sample, said process comprising: (a) isolating RNA from a sample; (b) preparing DNA from RNA by reverse transcriptase reaction and performing nucleic acid amplification reaction employing an oligonucleotide primer pair for amplifying a fragment in the presence of a probe capable of binding to the fragment, wherein the oligonucleotide primer pair is selected from the group consisting of a nucleic acid sequence as set forth in SEQ ID NO: 6 and SEQ ID NO: 7, SEQ ID NO: 8 and SEQ ID NO: 9, SEQ ID NO: 10 and SEQ ID NO: 11, SEQ ID NO: 12 and SEQ ID NO: 13, and SEQ ID NO: 14 and SEQ ID NO: 15, and wherein the probe having a nucleic acid sequence as set forth in SEQ ID NO: 18, or SEQ ID NO: 19, or SEQ ID NO: 20, or SEQ ID NO: 21, and a fluorophore and a quencher linked to the probe; and (c) detecting the presence or absence of the signal from the fluorophore, wherein the presence of the signal indicates the presence of SARS-CoV-2 in the sample.

In a fourth aspect of the present disclosure, there is provided an oligonucleotide primer pair selected from the group consisting of a nucleic acid sequence as set forth in SEQ ID NO: 6 and SEQ ID NO: 7, SEQ ID NO: 8 and SEQ ID NO: 9, SEQ ID NO: 6 and SEQ ID NO: 9, SEQ ID NO: 10 and SEQ ID NO: 11, SEQ ID NO: 12 and SEQ ID NO: 13, SEQ ID NO: 14 and SEQ ID NO: 15, SEQ ID NO: 16 and SEQ ID NO: 17, SEQ ID NO: 6 and SEQ ID NO: 13, SEQ ID NO: 6 and SEQ ID NO: 11, SEQ ID NO: 8 and SEQ ID NO: 11, SEQ ID NO: 8 and SEQ ID NO: 13, SEQ ID NO: 10 and SEQ ID NO: 13, and SEQ ID NO: 12 and SEQ ID NO: 11.

In a fifth aspect of the present disclosure, there is provided a probe having a fluorophore and a quencher linked to the probe, wherein the probe comprises a nucleic acid sequence of at least 20 nucleotides in length, and having at least 90% identity to the nucleic acid sequence as set forth in any one of SEQ ID NO: 1 or SEQ ID NO: 2 or SEQ ID NO: 3 or SEQ ID NO: 4 or SEQ ID NO: 5.

In a sixth aspect of the present disclosure, there is provided a kit comprising: (a) one or more oligonucleotide primers pair as described in the present disclosure; (b) a fluorescent dye; and (c) a buffer. The kit can further include dNTPs, DNA polymerase, Reverse transcriptase, internal reference control (ROX dye), nuclease-free water, random hexamer primer, GAPDH forward primer, GAPDH reverse primer, positive control (nucleic acid fragment), and no-template control.

In a seventh aspect of the present disclosure, there is provided a kit comprising: (a) one or more oligonucleotide primer pairs as described in the present disclosure; (b) one or more probes as described in the present disclosure; and (c) a buffer. The kit can further include dNTPs, DNA polymerase, Reverse transcriptase, internal reference control (ROX dye), nuclease-free water, random hexamer primer, GAPDH forward primer, GAPDH reverse primer, positive control (nucleic acid fragment), and no-template control.

In an eighth aspect of the present disclosure, there is provided a use of a nucleic acid fragment having a nucleic acid sequence with at least 95% identity to the nucleic acid sequence as set forth in any one of SEQ ID NO: 1 or SEQ ID NO: 2 or SEQ ID NO: 3 or SEQ ID NO: 4 or SEQ ID NO: 5 for developing vaccine against SARS-CoV-2.

In a ninth aspect of the present disclosure, there is provided a use of a nucleic acid fragment having a nucleic acid sequence as set forth in any one of SEQ ID NO: 1 or SEQ ID NO: 2 or SEQ ID NO: 3 or SEQ ID NO: 4 or SEQ ID NO: 5 for developing vaccine against SARS-CoV-2.

In a tenth aspect of the present disclosure, there is provided a use of the oligonucleotide primer pairs as described in the present disclosure for sequencing a region of SARS-CoV-2.

In an eleventh aspect of the present disclosure, there is provided a use of the oligonucleotide primer pairs as described in the present disclosure for detecting the presence of SARS-CoV-2 in a sample.

In a twelfth aspect of the present disclosure, there is provided a use of a nucleic acid fragment having a nucleic acid sequence with at least 95% identity to the nucleic acid sequence as set forth in any one of SEQ ID NO: 1 or SEQ ID NO: 2 or SEQ ID NO: 3 or SEQ ID NO: 4 or SEQ ID NO: 5 for drug development against SARS-CoV-2.

In a thirteenth aspect of the present disclosure, there is provided a use of a nucleic acid fragment having a nucleic acid sequence with at least 95% identity to the nucleic acid sequence as set forth in any one of SEQ ID NO: 1 or SEQ ID NO: 2 or SEQ ID NO: 3 or SEQ ID NO: 4 or SEQ ID NO: 5 for detecting the presence of SARS-CoV-2 in a sample.

In a fourteenth aspect of the present disclosure, there is provided a nucleic acid fragment having a nucleic acid sequence with at least 95% identity to the nucleic acid sequence as set forth in any one of SEQ ID NO: 1 or SEQ ID NO: 2 or SEQ ID NO: 3 or SEQ ID NO: 4 or SEQ ID NO: 5.

These and other features, aspects, and advantages of the present subject matter will be better understood with reference to the following description and appended claims. This summary is provided to introduce a selection of concepts in a simplified form. This summary is not intended to identify key features or essential features of the claimed subject matter, nor is it intended to be used to limit the scope of the claimed subject matter.

BRIEF DESCRIPTION OF ACCOMPANYING DRAWINGS

The following drawings form a part of the present specification and are included to further illustrate aspects of the present disclosure. The disclosure may be better understood by reference to the drawings in combination with the detailed description of the specific embodiments presented herein.

FIG. 1 depicts a schematic representation of the oligonucleotide primer pairs and their binding regions on the gene S (ORF 1AB) of the SARS-CoV-2 genome, in accordance with an embodiment of the present disclosure.

Figure 3:
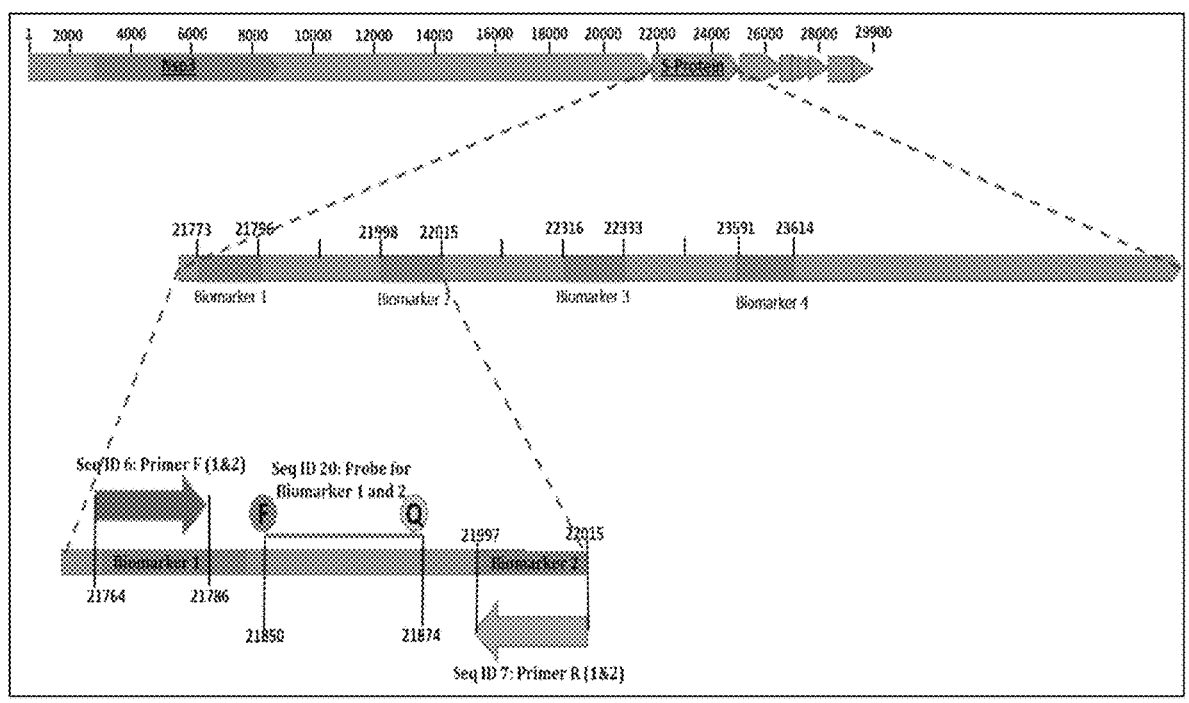

FIG. 3 depicts a schematic representation of COVID-19 virus genome portion depicting coding stretch for the S-Protein. The genomic positions of Biomarkers 1 & 2 and Probe (SEQ ID NO: 20) and the forward (SEQ ID NO: 6) and reverse (SEQ ID NO: 7) primer sequence for amplification of these Biomarkers are shown, in accordance with an embodiment of the present disclosure.

FIG. 4 depicts a schematic representation of COVID-19 virus genome portion depicting coding stretch for the S-Protein. The genomic positions of Biomarker 3 and the forward (SEQ ID NO: 8) and reverse (SEQ ID NO: 9) primer sequence for amplification of this Biomarker are shown, in accordance with an embodiment of the present disclosure.

FIG. 5 depicts a schematic representation of COVID-19 virus genome portion depicting coding stretch for the S-Protein. The genomic positions of Biomarker 3 and Probe (SEQ ID NO: 21) and the forward (SEQ ID NO: 8) and reverse (SEQ ID NO: 9) primer sequence for amplification of this Biomarker are shown, in accordance with an embodiment of the present disclosure.

FIG. 6 depicts a schematic representation of COVID-19 virus genome portion depicting coding stretch for the S-Protein. The genomic positions of Biomarker 4 and the forward (SEQ ID NO: 10) and reverse (SEQ ID NO: 11) primer sequence for amplification of this Biomarker are shown, in accordance with an embodiment of the present disclosure.

FIG. 7 depicts a schematic representation of COVID-19 virus genome portion depicting coding stretch for the S-Protein. The genomic positions of Biomarker 4 and Probe (SEQ ID NO: 18) and the forward (SEQ ID NO: 12) and reverse (SEQ ID NO: 13) primer sequence for amplification of this Biomarker are shown, in accordance with an embodiment of the present disclosure.

FIG. 8 depicts a schematic representation of COVID-19 virus genome portion depicting coding stretch for the Nsp3-Protein. The genomic positions of Biomarker 5 and the forward (SEQ ID NO: 16) and reverse (SEQ ID NO: 17) primer sequence for amplification of this Biomarkers are shown, in accordance with an embodiment of the present disclosure.

FIG. 9 depicts a schematic representation of COVID-19 virus genome portion depicting coding stretch for the Nsp-Protein. The genomic positions of Biomarker 5 and Probe (SEQ ID 19) and the forward (SEQ ID NO: 14) and reverse (SEQ ID NO: 15) primer sequence for amplification of this Biomarker are shown, in accordance with an embodiment of the present disclosure.

FIG. 10 depicts a schematic representation of COVID-19 virus genome portion depicting coding stretches for protein sequences Nsp3 and S-Protein. The genomic positions of biomarkers and the forward and reverse primer sequence for amplification for each biomarker used in probe-free (SYBR Green-based) RT-PCR are shown. Also shown are the fluorescent probes (F—fluorophore and Q—quencher) and respective forward and reverse primers used in their amplification in (TaqMan) probe-based RT-PCR. The numbers in each box are the SEQ IDs of each listed sequence.

Figure 11:
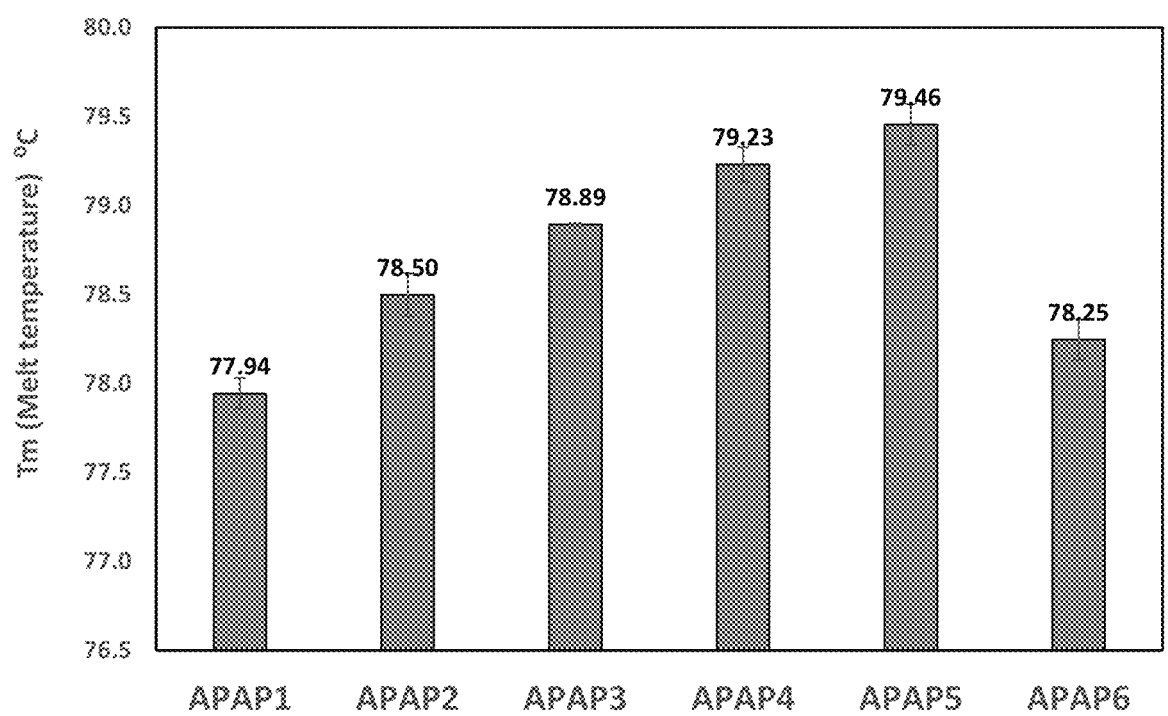

FIG. 11 depicts a schematic representation of melting temperatures of the different oligonucleotide primer pairs APAP 1 to APAP 6 used for PCR based detection for the presence of SARS-CoV-2.

DETAILED DESCRIPTION OF THE INVENTION

Those skilled in the art will be aware that the present disclosure is subject to variations and modifications other than those specifically described. It is to be understood that the present disclosure includes all such variations and modifications. The disclosure also includes all such steps, features, compositions, and compounds referred to or indicated in this specification, individually or collectively, and any and all combinations of any or more of such steps or features.

Definitions

For convenience, before further description of the present disclosure, certain terms employed in the specification, and examples are delineated here. These definitions should be read in the light of the remainder of the disclosure and understood as by a person of skill in the art. The terms used herein have the meanings recognized and known to those of skill in the art, however, for convenience and completeness, particular terms and their meanings are set forth below.

The articles "a", "an" and "the" are used to refer to one or to more than one (i.e., to at least one) of the grammatical object of the article.

The terms "comprise" and "comprising" are used in the inclusive, open sense, meaning that additional elements may be included. It is not intended to be construed as "consists of only".

Throughout this specification, unless the context requires otherwise the word "comprise", and variations such as "comprises" and "comprising", will be understood to imply the inclusion of a stated element or step or group of element or steps but not the exclusion of any other element or step or group of element or steps.

The term "including" is used to mean "including but not limited to". "Including" and "including but not limited to" are used interchangeably.

Unless defined otherwise, all technical and scientific terms used herein have the same meaning as commonly understood by one of ordinary skill in the art to which this disclosure belongs. Although any methods and materials similar or equivalent to those described herein can be used in the practice or testing of the disclosure, the preferred methods, and materials are now described. All publications mentioned herein are incorporated herein by reference.

For the purpose of the present disclosure, the term "COVID-19" refers to the novel coronavirus strain that was first reported from China. The nomenclature of the virus has changed over the last two months, first it was named "Wuhan sea-food virus", then it was named "nCoV-2019" or "2019-nCoV". Subsequently, it was renamed as "COVID-19 virus" or "severe acute respiratory syndrome coronavirus 2" or "SARS-CoV-2". This clarity has been provided to avoid any inconsistencies arising from usage of different names for the same virus.

The term "PCR" refers to polymerase chain reaction which is well-known method to amplify nucleic acid of interest. The polymerase chain reaction (PCR) amplification of nucleic acids is regularly performed using fluorescently labelled oligonucleotide primers to produce an amplified DNA product that can be detected and quantified absolutely. A wide range of fluorophores are commercially available with spectral characteristics ($\lambda_{max}$ excitation and $\lambda_{max}$ emission) covering the wavelength range 350 to 700 nm, and into the near infra-red region of the electromagnetic spectrum. Thus, simultaneous, multiple detection of labelled molecules can be performed on the same sample, for example, following 'multiplex' PCR amplification of several nucleic acid sequences using pairs of oligonucleotide primers labelled with different fluorophores. Each pair gives rise to a separate amplified product that can be unambiguously identified due to its fluorescent label. The term "real-time polymerase chain reaction" or "real-time PCR", also known as quantitative polymerase chain reaction (qPCR), is a laboratory technique of molecular biology based on the polymerase chain reaction (PCR). The technique monitors the amplification of a targeted DNA molecule during the PCR. Real-time PCR can be used quantitatively (quantitative real-time PCR) and semi-quantitatively (i.e., above/below a certain amount of DNA molecules) (semi-quantitative real-time PCR).

The term "nucleic acid" refers to either deoxyribonucleic acid (DNA), ribonucleic acid (RNA), single-stranded or double-stranded and any chemical modifications thereof. Nucleic acids can be of any size and are preferably oligonucleotides. Modifications include, but are not limited to, those that provide other chemical groups that incorporate additional charge, polarizability, hydrogen bonding, electrostatic interaction, and functionality to the individual nucleic acid bases or to the nucleic acid as a whole. The nucleic acid can be derived from a completely chemical synthesis process, such as a solid phase mediated chemical synthesis, or from a biological origin, such as through isolation from almost any species that can provide DNA or RNA, or from processes that involve the manipulation of nucleic acids by molecular biology tools, such as DNA replication, PCR amplification, reverse transcription, or from a combination of those processes. Any possible modification of the nucleic acid and nucleic acids of virtually any origin are contemplated by the present disclosure.

The term "fluorescent dye" refers to a dye that emits electromagnetic radiation of longer wavelength by a fluorescence mechanism upon irradiation by a source of electromagnetic radiation, including but not limited to a lamp, a photodiode or a laser.

The term "primer" refers to the nucleic acid which is complementary to each strand of nucleotide sequence to be amplified. As per the present disclosure, the primers are also referred to as "oligonucleotide primer". The term "oligonucleotide primer pair" or "primer set" refers to the particular pair of primers that could be used for the successful detection of the virus. The present disclosure discloses numerous primers, however, it is a common knowledge that only specific pairs of primers would provide the desired result.

The term "probe" refers to a nucleic acid that carries a multitude of covalently attached dyes, with at least one of the dyes being fluorescent (also referred to as a fluorophore). As per the present disclosure, the other dye being a quencher. The quencher molecule results in quenching of the fluorescence emitted by the fluorophore when present in close proximity.

The term "sample" refers to any known types of samples that are collected from patients to be tested for the presence of COVID-19. As per the present disclosure, a non-limiting list of samples are sputum, blood, swab, lung biopsy, pleural fluid, and tracheal aspirate. The sample thus obtained is to be used for preparing nucleic acid by any known techniques. The obtained nucleic acid is further used as a template for performing PCR for detection of SARS-CoV-2.

The term "Reverse Transcriptase PCR" refers to use of reverse transcriptase enzyme in a PCR reaction which is well practised in the art for converting RNA into DNA for further analyses.

The term "RT-PCR" refers to Real-Time Polymerase Chain reaction which is well practiced for simultaneous and quantitative detection of the amplified DNA during the reaction.

The term "amplicon" refers to the nucleic acid that is amplified using an oligonucleotide primer pair. The amplicon fragment thus obtained can be tested by any known techniques in the art.

The term "biomarker" relates to a specific nucleic acid fragment which can relate to a particular pathological or physiological or a specific condition in a subject.

The present disclosure provides biomarkers, oligonucleotide primer pairs, and probes for detecting the presence of SARS-CoV-2 in a sample. The present disclosure provides the primer pairs which are specific and sensitive for the detection of SARS-CoV-2 in a sample. Owing to the highly specific nature, the present disclosure discloses a probe-free PCR based method for the detection of SARS-CoV-2. Given the rampant spread of SARS-CoV-2 across the globe, the detection method should be economically and commercially viable so that massive upscaling is not a hindrance for enabling large scale assays for the detection of the virus. The probe-free method as disclosed in the present disclosure satisfies the requirement and is an attractive method for the detection of SARS-CoV-2 without leveraging the specificity and sensitivity. The present disclosure also discloses probe-based methods along with different probes for using with different primer pairs which can be used for a reliable detection of SARS-CoV-2. Further, the present disclosure discloses biomarkers which can be used for detecting the SARS-CoV-2, and used as a target for developing vaccine against the virus, and for drug development. The oligonucleotide primer pairs as disclosed herein can be used in detecting the presence of SARS-CoV-2, and for sequencing a region of the virus. The probes as disclosed herein can be used for detecting the presence of the virus in a sample. Furthermore, the biomarkers, and the probes as disclosed herein can be used for raising antibodies against COVID-19 which further can be used for antibody-based detection of COVID-19. The primers as disclosed herein can also be used for performing multiplex PCR in which more than one primer pair is used for detecting the presence of more than one amplicon. The present disclosure also discloses a nucleic acid fragment having a nucleic acid sequence at least 95% identical to the nucleic acid sequence as set forth in SEQ ID NO: 1, or SEQ ID NO: 2, or SEQ ID NO: 3, or SEQ ID NO: 4, or SEQ ID NO: 5.

In an embodiment of the present disclosure, there is provided a process for detecting the presence of SARS-CoV-2 in a sample, said process comprising: (a) isolating RNA from a sample; (b) preparing DNA from RNA by reverse transcriptase reaction and performing nucleic acid amplification reaction employing an oligonucleotide primer pair to produce an amplicon, wherein the set of primer pairs is selected from the group consisting of a nucleic acid sequence as set forth in SEQ ID NO: 6 and SEQ ID NO: 7, SEQ ID NO: 8 and SEQ ID NO: 9, SEQ ID NO: 6 and SEQ ID NO: 9, SEQ ID NO: 10 and SEQ ID NO: 11, SEQ ID NO: 12 and SEQ ID NO: 13, SEQ ID NO: 14 and SEQ ID NO: 15, SEQ ID NO: 16 and SEQ ID NO: 17, SEQ ID NO: 6 and SEQ ID NO: 13, SEQ ID NO: 6 and SEQ ID NO: 11, SEQ ID NO: 8 and SEQ ID NO: 11, SEQ ID NO: 8 and SEQ ID NO: 13, SEQ ID NO: 10 and SEQ ID NO: 13, and SEQ ID NO: 12 and SEQ ID NO: 11; and (c) detecting the presence or absence of the amplicon, wherein the presence of the amplicon indicates the presence of SARS-CoV-2 in the sample.

In an embodiment of the present disclosure, there is provided a process for detecting the presence of SARS-CoV-2 in a sample as described herein, wherein the sample is selected from the group consisting of sputum, blood, swab, lung biopsy, pleural fluid, and tracheal aspirate.

In an embodiment of the present disclosure, there is provided a process for detecting the presence of SARS-CoV-2 in a sample as described herein, wherein detecting the presence or absence of the amplicon is done using a fluorescent dye.

In an embodiment of the present disclosure, there is provided a process for detecting the presence of SARS-CoV-2 in a sample as described herein, wherein detecting the presence or absence of the amplicon is done using a fluorescent dye, and wherein the fluorescent dye is selected from the group consisting of SYBR Green, EvaGreen, SYTO-13, SYTO-16, SYTO-80, SYTO-82, and BEBO. In another embodiment, the fluorescent dye is SYBR Green. In yet another embodiment, the fluorescent dye is EvaGreen. In an alternate embodiment, the fluorescent dye is BEBO.

In an embodiment of the present disclosure, there is provided a process for detecting the presence of SARS-CoV-2 in a sample as described herein, wherein the set of primer pair is having a nucleic acid sequence as set forth in SEQ ID NO: 6 and SEQ ID NO: 7.

In an embodiment of the present disclosure, there is provided a process for detecting the presence of SARS-CoV-2 in a sample as described herein, wherein the set of primer pair is having a nucleic acid sequence as set forth in SEQ ID NO: 8 and SEQ ID NO: 9.

In an embodiment of the present disclosure, there is provided a process for detecting the presence of SARS-CoV-2 in a sample as described herein, wherein the set of primer pair is having a nucleic acid sequence as set forth in SEQ ID NO: 10 and SEQ ID NO: 11.

In an embodiment of the present disclosure, there is provided a process for detecting the presence of SARS-CoV-2 in a sample as described herein, wherein the set of primer pair is having a nucleic acid sequence as set forth in SEQ ID NO: 12 and SEQ ID NO: 13.

In an embodiment of the present disclosure, there is provided a process for detecting the presence of SARS-CoV-2 in a sample as described herein, wherein the set of primer pair is having a nucleic acid sequence as set forth in SEQ ID NO: 14 and SEQ ID NO: 15.

In an embodiment of the present disclosure, there is provided a process for detecting the presence of SARS-CoV-2 in a sample as described herein, wherein the set of primer pair is having a nucleic acid sequence as set forth in SEQ ID NO: 16 and SEQ ID NO: 17.

In an embodiment of the present disclosure, there is provided a process for detecting the presence of SARS-CoV-2 in a sample, said process comprising: (a) preparing nucleic acid from a sample; (b) performing nucleic acid amplification reaction employing the nucleic acid of step (a)

and one or more oligonucleotide primer pairs for producing one or more amplicons, wherein the amplicon comprises a nucleic acid sequence selected from the group consisting of SEQ ID NO: 1, SEQ ID NO: 2, SEQ ID NO: 3, SEQ ID NO: 4, and SEQ ID NO: 5; and (c) detecting the presence or absence of one or more amplicons, wherein the presence of one or more amplicons indicates the presence of SARS-CoV-2 in the sample.

In an embodiment of the present disclosure, there is provided a process for detecting the presence of SARS-CoV-2 in a sample, said process comprising: (a) preparing nucleic acid from a sample; (b) performing nucleic acid amplification reaction employing the nucleic acid of step (a) and one or more oligonucleotide primer pairs for producing one or more amplicons, wherein the amplicon comprises a nucleic acid sequence selected from the group consisting of SEQ ID NO: 1, SEQ ID NO: 2, SEQ ID NO: 3, SEQ ID NO: 4, and SEQ ID NO: 5; and (c) detecting the presence or absence of one or more amplicons, wherein the presence of one or more amplicons indicates the presence of SARS-CoV-2 in the sample, and wherein the oligonucleotide primer pair consisting of a first primer having a nucleic acid sequence as set forth in SEQ ID NO: 6, and a second primer having a nucleic acid sequence as set forth in SEQ ID NO: 7, is used for producing the amplicon comprising a nucleic acid sequence as set forth in SEQ ID NO: 1, or SEQ ID NO: 2.

In an embodiment of the present disclosure, there is provided a process for detecting the presence of SARS-CoV-2 in a sample, said process comprising: (a) preparing nucleic acid from a sample; (b) performing nucleic acid amplification reaction employing the nucleic acid of step (a) and one or more oligonucleotide primer pairs for producing one or more amplicons, wherein the amplicon comprises a nucleic acid sequence selected from the group consisting of SEQ ID NO: 1, SEQ ID NO: 2, SEQ ID NO: 3, SEQ ID NO: 4, and SEQ ID NO: 5; and (c) detecting the presence or absence of one or more amplicons, wherein the presence of one or more amplicons indicates the presence of SARS-CoV-2 in the sample, and wherein the oligonucleotide primer pair consisting of a first primer having a nucleic acid sequence as set forth in SEQ ID NO: 8, and a second primer having a nucleic acid sequence as set forth in SEQ ID NO: 9, is used for producing the amplicon comprising a nucleic acid sequence as set forth in SEQ ID NO: 3.

In an embodiment of the present disclosure, there is provided a process for detecting the presence of SARS-CoV-2 in a sample, said process comprising: (a) preparing nucleic acid from a sample; (b) performing nucleic acid amplification reaction employing the nucleic acid of step (a) and one or more oligonucleotide primer pairs for producing one or more amplicons, wherein the amplicon comprises a nucleic acid sequence selected from the group consisting of SEQ ID NO: 1, SEQ ID NO: 2, SEQ ID NO: 3, SEQ ID NO: 4, and SEQ ID NO: 5; and (c) detecting the presence or absence of one or more amplicons, wherein the presence of one or more amplicons indicates the presence of SARS-CoV-2 in the sample, and wherein the oligonucleotide primer pair consisting of a first primer having a nucleic acid sequence as set forth in SEQ ID NO: 10, and a second primer having a nucleic acid sequence as set forth in SEQ ID NO: 11, or a first primer having a nucleic acid sequence as set forth in SEQ ID NO: 12, and a second primer having a nucleic acid sequence as set forth in SEQ ID NO: 13, is used for producing the amplicon comprising a nucleic acid sequence as set forth in SEQ ID NO: 4.

In an embodiment of the present disclosure, there is provided a process for detecting the presence of SARS-CoV-2 in a sample, said process comprising: (a) preparing nucleic acid from a sample; (b) performing nucleic acid amplification reaction employing the nucleic acid of step (a) and one or more oligonucleotide primer pairs for producing one or more amplicons, wherein the amplicon comprises a nucleic acid sequence selected from the group consisting of SEQ ID NO: 1, SEQ ID NO: 2, SEQ ID NO: 3, SEQ ID NO: 4, and SEQ ID NO: 5; and (c) detecting the presence or absence of one or more amplicons, wherein the presence of one or more amplicons indicates the presence of SARS-CoV-2 in the sample, and wherein the oligonucleotide primer pair consisting of a first primer having a nucleic acid sequence as set forth in SEQ ID NO: 14, and a second primer having a nucleic acid sequence as set forth in SEQ ID NO: 15, or a first primer having a nucleic acid sequence as set forth in SEQ ID NO: 16 and a second primer having a nucleic acid sequence as set forth in SEQ ID NO: 17, is used for producing the amplicon comprising a nucleic acid sequence as set forth in SEQ ID NO: 5.

In an embodiment of the present disclosure, there is provided a process for detecting the presence of SARS-CoV-2 in a sample, wherein preparing nucleic acid from the sample comprises: (a) isolating RNA from the sample; and (b) performing reverse transcriptase reaction to obtain DNA.

In an embodiment of the present disclosure, there is provided a process for detecting the presence of SARS-CoV-2 in a sample, said process comprising: (a) isolating RNA from a sample; (b) preparing DNA from RNA by reverse transcriptase reaction and performing nucleic acid amplification reaction employing an oligonucleotide primer pair for amplifying a fragment in the presence of a probe capable of binding to the fragment, wherein the oligonucleotide primer pair is selected from the group consisting of a nucleic acid sequence as set forth in SEQ ID NO: 6 and SEQ ID NO: 7, SEQ ID NO: 8 and SEQ ID NO: 9, SEQ ID NO: 10 and SEQ ID NO: 11, SEQ ID NO: 12 and SEQ ID NO: 13, and SEQ ID NO: 14 and SEQ ID NO: 15, and wherein the probe having a nucleic acid sequence as set forth in SEQ ID NO: 18, or SEQ ID NO: 19, or SEQ ID NO: 20, or SEQ ID NO: 21, and a fluorophore and a quencher linked to the probe; and (c) detecting the presence or absence of the signal from the fluorophore, wherein the presence of the signal indicates the presence of SARS-CoV-2 in the sample.

In an embodiment of the present disclosure, there is provided a process for detecting the presence of SARS-CoV-2 in a sample, said process comprising: (a) isolating RNA from a sample; (b) preparing DNA from RNA by reverse transcriptase reaction and performing nucleic acid amplification reaction employing an oligonucleotide primer pair for amplifying a fragment in the presence of a probe capable of binding to the fragment, wherein the oligonucleotide primer pair is as set forth in SEQ ID NO: 6 and SEQ ID NO: 7, and wherein the probe is having a nucleic acid sequence as set forth in SEQ ID NO: 20, and a fluorophore and a quencher linked to the probe; and (c) detecting the presence or absence of the signal from the fluorophore, wherein the presence of the signal indicates the presence of SARS-CoV-2 in the sample.

In an embodiment of the present disclosure, there is provided a process for detecting the presence of SARS-CoV-2 in a sample, said process comprising: (a) isolating RNA from a sample; (b) preparing DNA from RNA by reverse transcriptase reaction and performing nucleic acid amplification reaction employing an oligonucleotide primer pair for amplifying a fragment in the presence of a probe capable of binding to the fragment, wherein the oligonucleotide primer pair is as set forth in SEQ ID NO: 8 and SEQ ID NO: 9, and wherein the probe is having a nucleic acid sequence as set forth in SEQ ID NO: 21, and a fluorophore and a quencher linked to the probe; and (c) detecting the presence or absence of the signal from the fluorophore, wherein the presence of the signal indicates the presence of SARS-CoV-2 in the sample.

In an embodiment of the present disclosure, there is provided a process for detecting the presence of SARS-CoV-2 in a sample, said process comprising: (a) isolating RNA from a sample; (b) preparing DNA from RNA by reverse transcriptase reaction and performing nucleic acid amplification reaction employing an oligonucleotide primer pair for amplifying a fragment in the presence of a probe capable of binding to the fragment, wherein the oligonucleotide primer pair is as set forth in SEQ ID NO: 10 and SEQ ID NO: 11, or SEQ ID NO: 12 and SEQ ID NO: 13, and wherein the probe is having a nucleic acid sequence as set forth in SEQ ID NO: 18, and a fluorophore and a quencher linked to the probe; and (c) detecting the presence or absence of the signal from the fluorophore, wherein the presence of the signal indicates the presence of SARS-CoV-2 in the sample.

In an embodiment of the present disclosure, there is provided a process for detecting the presence of SARS-CoV-2 in a sample, said process comprising: (a) isolating RNA from a sample; (b) preparing DNA from RNA by reverse transcriptase reaction and performing nucleic acid amplification reaction employing an oligonucleotide primer pair for amplifying a fragment in the presence of a probe capable of binding to the fragment, wherein the oligonucleotide primer pair is as set forth in SEQ ID NO: 14 and SEQ ID NO: 15, and wherein the probe is having a nucleic acid sequence as set forth in SEQ ID NO: 19, and a fluorophore and a quencher linked to the probe; and (c) detecting the presence or absence of the signal from the fluorophore, wherein the presence of the signal indicates the presence of SARS-CoV-2 in the sample.

In an embodiment of the present disclosure, there is provided a process for detecting the presence of SARS-CoV-2 in a sample, wherein the fluorophore and the quencher is selected from the group consisting of FAM and BHQ0, FAM and BHQ1 HEX and BHQ1, CY5 and BHQ3, FAM and TAMRA, and TET and TAMRA. In another embodiment, the fluorophore and the quencher is FAM and BHQ0. In yet another embodiment, the fluorophore and the quencher is FAM and BHQ1. In yet another embodiment, the fluorophore and the quencher is HEX and BHQ1. In still another embodiment, the fluorophore and the quencher is CY5 and BHQ3. In an alternate embodiment, the fluorophore and the quencher is FAM and TAMRA. In a different embodiment, the fluorophore and the quencher is TET and TAMRA.

In an embodiment of the present disclosure, there is provided a process for detecting the presence of SARS-CoV-2 in a sample, wherein the fluorophore and the quencher is selected from the group consisting of FAM and BHQ0, HEX and BHQ1, CY5 and BHQ3, FAM and TAMRA, and TET and TAMRA, Alexa 350-Dabcyl, Pacific Blue-Dabcyl, Marina Blue-Dabcyl, Acridine-Dabcyl, Edans-Dabcyl, Coumarin-Dabcyl, BODIPY 493/513-Dabcyl, Cy2-Dabcyl, BODIPY FL-X-Dabcyl, DANSYL-Dabcyl, Alexa 488-BHQ1, FAM-BHQ1, Oregon Green-BHQ1, Rhodamine Green X-BHQ1, NBD X-BHQ1, TET-BHQ1, Alexa-430-BHQ1, BODIPY R6GX-BHQ1, Joe-BHQ1, Yakima Yellow-BHQ1, Alexa 532-BHQ1, VIC-BHQ1, HEX-BHQ1, R6G-BHQ2, Alexa 555-BHQ2, BODIPY 564/570-BHQ2, BODIPY TMR-X-BHQ2, Cy3-BHQ2, Alexa 546-BHQ2, TAMRA-BHQ2, Rhodamine Red X-BHQ2, BODIPY 581/591-BHQ2, Redmond Red-BHQ2, Cy3.5-BHQ2, ROX-BHQ2, Alexa 568-BHQ2, Cal Red-BHQ2, BIODIPY TR-X-BHQ2, Alexa 594-BHQ2, BIODIPY 630/650 X-BHQ2, LC Red 640-BBQ-650, Alexa 633-BBQ-650, BIODIPY 650/655 X-BBQ-650, Alexa 647-BBQ-650, Cy5-BBQ-650, Alexa 660-BBQ-650, Cy5.5-BBQ-650, Alexa 680-BBQ-650, LC Red 705-BBQ-650, Alexa 700-BBQ-650, and Alexa 750-BBQ-650.

In an embodiment of the present disclosure, there is provided an oligonucleotide primer pair selected from the group consisting of a nucleic acid sequence as set forth in SEQ ID NO: 6 and SEQ ID NO: 7, SEQ ID NO: 8 and SEQ ID NO: 9, SEQ ID NO: 6 and SEQ ID NO: 9, SEQ ID NO: 10 and SEQ ID NO: 11, SEQ ID NO: 12 and SEQ ID NO: 13, SEQ ID NO: 14 and SEQ ID NO: 15, SEQ ID NO: 16 and SEQ ID NO: 17, SEQ ID NO: 6 and SEQ ID NO: 13, SEQ ID NO: 6 and SEQ ID NO: 11, SEQ ID NO: 8 and SEQ ID NO: 11, SEQ ID NO: 8 and SEQ ID NO: 13, SEQ ID NO: 10 and SEQ ID NO: 13, and SEQ ID NO: 12 and SEQ ID NO: 11.

In an embodiment of the present disclosure, there is provided an oligonucleotide primer pair having a nucleic acid sequence as set forth in SEQ ID NO: 6 and SEQ ID NO: 7.

In an embodiment of the present disclosure, there is provided an oligonucleotide primer pair having a nucleic acid sequence as set forth in SEQ ID NO: 8 and SEQ ID NO: 9.

In an embodiment of the present disclosure, there is provided an oligonucleotide primer pair having a nucleic acid sequence as set forth in SEQ ID NO: 10 and SEQ ID NO: 11.

In an embodiment of the present disclosure, there is provided an oligonucleotide primer pair having a nucleic acid sequence as set forth in SEQ ID NO: 12 and SEQ ID NO: 13.

In an embodiment of the present disclosure, there is provided an oligonucleotide primer pair having a nucleic acid sequence as set forth in SEQ ID NO: 14 and SEQ ID NO: 15.

In an embodiment of the present disclosure, there is provided an oligonucleotide primer pair having a nucleic acid sequence as set forth in SEQ ID NO: 16 and SEQ ID NO: 17.

In an embodiment of the present disclosure, there is provided an oligonucleotide primer pair having a nucleic acid sequence as set forth in SEQ ID NO: 6 and SEQ ID NO: 13.

In an embodiment of the present disclosure, there is provided an oligonucleotide primer pair having a nucleic acid sequence as set forth in SEQ ID NO: 6 and SEQ ID NO: 11.

In an embodiment of the present disclosure, there is provided an oligonucleotide primer pair having a nucleic acid sequence as set forth in SEQ ID NO: 8 and SEQ ID NO: 11.

In an embodiment of the present disclosure, there is provided an oligonucleotide primer pair having a nucleic acid sequence as set forth in SEQ ID NO: 8 and SEQ ID NO: 13.

In an embodiment of the present disclosure, there is provided a probe having a fluorophore and a quencher linked to the probe, wherein the probe comprises a nucleic acid sequence of at least 20 nucleotides in length, and having at least 90%, or 91%, or 92%, or 93%, or 94%, or 95%, or 96%, or 97%, or 98%, or 99% or 99.5% or 99.75% or 100% identity to the nucleic acid sequence as set forth in any one of SEQ ID NO: 18, or SEQ ID NO: 19, or SEQ ID NO: 20, or SEQ ID NO: 21.

In an embodiment of the present disclosure, there is provided a probe having a fluorophore and a quencher linked to the probe, wherein the probe is having a nucleic acid sequence as set forth in SEQ ID NO: 18, or SEQ ID NO: 19, or SEQ ID NO: 20, or SEQ ID NO: 21.

In an embodiment of the present disclosure, there is provided a probe having a fluorophore and a quencher linked to the probe, wherein the probe is having a nucleic acid sequence as set forth in SEQ ID NO: 18.

In an embodiment of the present disclosure, there is provided a probe having a fluorophore and a quencher linked to the probe, wherein the probe is having a nucleic acid sequence as set forth in SEQ ID NO: 19.

In an embodiment of the present disclosure, there is provided a probe having a fluorophore and a quencher linked to the probe, wherein the probe is having a nucleic acid sequence as set forth in SEQ ID NO: 20.

In an embodiment of the present disclosure, there is provided a probe having a fluorophore and a quencher linked to the probe, wherein the probe is having a nucleic acid sequence as set forth in SEQ ID NO: 21.

In an embodiment of the present disclosure, there is provided a probe having a fluorophore and a quencher linked to the probe as described herein, wherein the fluorophore and the quencher is selected from the group consisting of FAM and BHQ0, HEX and BHQ1, CY5 and BHQ3, FAM and TAMRA, and TET and TAMRA, Alexa 350-Dabcyl, Pacific Blue-Dabcyl, Marina Blue-Dabcyl, Acridine-Dabcyl, Edans-Dabcyl, Coumarin-Dabcyl, BODIPY 493/513-Dabcyl, Cy2-Dabcyl, BODIPY FL-X-Dabcyl, DANSYL-Dabcyl, Alexa 488-BHQ1, FAM-BHQ1, Oregon Green-BHQ1, Rhodamine Green X-BHQ1, NBD X-BHQ1, TET-BHQ1, Alexa-430-BHQ1, BODIPY R6GX-BHQ1, Joe-BHQ1, Yakima Yellow-BHQ1, Alexa 532-BHQ1, VIC-BHQ1, HEX-BHQ1, R6G-BHQ2, Alexa 555-BHQ2, BODIPY 564/570-BHQ2, BODIPY TMR-X-BHQ2, Cy3-BHQ2, Alexa 546-BHQ2, TAMRA-BHQ2, Rhodamine Red X-BHQ2, BODIPY 581/591-BHQ2, Redmond Red-BHQ2, Cy3.5-BHQ2, ROX-BHQ2, Alexa 568-BHQ2, Cal Red-BHQ2, BIODIPY TR-X-BHQ2, Alexa 594-BHQ2, BIODIPY 630/650 X-BHQ2, LC Red 640-BBQ-650, Alexa 633-BBQ-650, BIODIPY 650/655 X-BBQ-650, Alexa 647-BBQ-650, Cy5-BBQ-650, Alexa 660-BBQ-650, Cy5.5-BBQ-650, Alexa 680-BBQ-650, LC Red 705-BBQ-650, Alexa 700-BBQ-650, and Alexa 750-BBQ-650.

In an embodiment of the present disclosure, there is provided a kit comprising: (a) one or more oligonucleotide primers pair as described in the present disclosure; (b) a fluorescent dye; and (c) a buffer.

In an embodiment of the present disclosure, there is provided a kit comprising: (a) one or more oligonucleotide primers pair as described in the present disclosure; (b) a fluorescent dye; and (c) a buffer, wherein the oligonucleotide primer pair is selected from the group consisting of a nucleic acid sequence as set forth in SEQ ID NO: 6 and SEQ ID NO: 7, SEQ ID NO: 8 and SEQ ID NO: 9, SEQ ID NO: 6 and SEQ ID NO: 9, SEQ ID NO: 10 and SEQ ID NO: 11, SEQ ID NO: 12 and SEQ ID NO: 13, SEQ ID NO: 14 and SEQ ID NO: 15, SEQ ID NO: 16 and SEQ ID NO: 17, SEQ ID NO: 6 and SEQ ID NO: 13, SEQ ID NO: 6 and SEQ ID NO: 11, SEQ ID NO: 8 and SEQ ID NO: 11, SEQ ID NO: 8 and SEQ ID NO: 13, SEQ ID NO: 10 and SEQ ID NO: 13, and SEQ ID NO: 12 and SEQ ID NO: 11.

In an embodiment of the present disclosure, there is provided a kit comprising: (a) one or more oligonucleotide primers pair as described in the present disclosure; (b) a fluorescent dye; and (c) a buffer, wherein the fluorescent dye is selected from the group consisting of SYBR Green, EvaGreen, SYTO-13, SYTO-16, SYTO-80, SYTO-82, and BEBO.

In an embodiment of the present disclosure, there is provided a kit comprising: (a) one or more oligonucleotide primers pair as described in the present disclosure; (b) a fluorescent dye; and (c) a buffer, wherein the buffer is selected from any one of the compatible buffer systems well known in the art.

In an embodiment of the present disclosure, there is provided a kit comprising: (a) one or more oligonucleotide primer pairs as described in the present disclosure; (b) one or more probes as described in the present disclosure; and (c) a buffer.

In an embodiment of the present disclosure, there is provided a kit comprising: (a) one or more oligonucleotide primer pairs as described in the present disclosure; (b) one or more probes as described in the present disclosure; and (c) a buffer, wherein the oligonucleotide primer pair is selected from the group consisting of a nucleic acid sequence as set forth in SEQ ID NO: 6 and SEQ ID NO: 7, SEQ ID NO: 8 and SEQ ID NO: 9, SEQ ID NO: 6 and SEQ ID NO: 9, SEQ ID NO: 10 and SEQ ID NO: 11, SEQ ID NO: 12 and SEQ ID NO: 13, SEQ ID NO: 14 and SEQ ID NO: 15, SEQ ID NO: 16 and SEQ ID NO: 17, SEQ ID NO: 6 and SEQ ID NO: 13, SEQ ID NO: 6 and SEQ ID NO: 11, SEQ ID NO: 8 and SEQ ID NO: 11, SEQ ID NO: 8 and SEQ ID NO: 13, SEQ ID NO: 10 and SEQ ID NO: 13, and SEQ ID NO: 12 and SEQ ID NO: 11.

In an embodiment of the present disclosure, there is provided a kit comprising: (a) one or more oligonucleotide primer pairs as described in the present disclosure; (b) one or more probes as described in the present disclosure; and (c) a buffer, wherein the probe is having a fluorophore and a quencher linked to the probe, and wherein the probe comprises a nucleic acid sequence of at least 20 nucleotides in length, and having at least 90% identity to the nucleic acid sequence as set forth in any one of SEQ ID NO: 18 or SEQ ID NO: 19 or SEQ ID NO: 20 or SEQ ID NO: 21 In yet another embodiment, the fluorophore and the quencher is any well-known combination for the purposes of PCR detection.

In an embodiment of the present disclosure, there is provided a use of a nucleic acid fragment having a nucleic acid sequence with at least 95% identity to the nucleic acid sequence as set forth in any one of SEQ ID NO: 1 or 2 or 3 or 4 or 5 as a target for developing vaccine against SARS-CoV-2. In another embodiment, there is provided a use of a nucleic acid fragment having a nucleic acid sequence with at least 95%, or 96%, or 97%, or 98%, or 99%, or 99.5% identity to the nucleic acid sequence as set forth in any one of SEQ ID NO: 1 or 2 or 3 or 4 or 5 as a target for developing vaccine against SARS-CoV-2.

In an embodiment of the present disclosure, there is provided a use of a nucleic acid fragment having a nucleic acid sequence with at least 95%, or 96%, or 97%, or 98%, or 99%, or 99.5% identity to the nucleic acid sequence as set forth in SEQ ID NO: 1 as a target for developing vaccine against SARS-CoV-2.

In an embodiment of the present disclosure, there is provided a use of a nucleic acid fragment having a nucleic acid sequence with at least 95%, or 96%, or 97%, or 98%, or 99%, or 99.5% identity to the nucleic acid sequence as set forth in SEQ ID NO: 2 as a target for developing vaccine against SARS-CoV-2.

In an embodiment of the present disclosure, there is provided a use of a nucleic acid fragment having a nucleic acid sequence with at least 95%, or 96%, or 97%, or 98%, or 99%, or 99.5% identity to the nucleic acid sequence as set forth in SEQ ID NO: 3 as a target for developing vaccine against SARS-CoV-2.

In an embodiment of the present disclosure, there is provided a use of a nucleic acid fragment having a nucleic acid sequence with at least 95%, or 96%, or 97%, or 98%, or 99%, or 99.5% identity to the nucleic acid sequence as set forth in SEQ ID NO: 4 as a target for developing vaccine against SARS-CoV-2.

In an embodiment of the present disclosure, there is provided a use of a nucleic acid fragment having a nucleic acid sequence with at least 95%, or 96%, or 97%, or 98%, or 99%, or 99.5% identity to the nucleic acid sequence as set forth in SEQ ID NO: 5 as a target for developing vaccine against SARS-CoV-2.

In an embodiment of the present disclosure, there is provided a use of a nucleic acid fragment having a nucleic acid sequence as set forth in SEQ ID NO: 1 for developing vaccine against SARS-CoV-2.

In an embodiment of the present disclosure, there is provided a use of a nucleic acid fragment having a nucleic acid sequence as set forth in SEQ ID NO: 2 for developing vaccine against SARS-CoV-2.

In an embodiment of the present disclosure, there is provided a use of a nucleic acid fragment having a nucleic acid sequence as set forth in SEQ ID NO: 3 for developing vaccine against SARS-CoV-2.

In an embodiment of the present disclosure, there is provided a use of a nucleic acid fragment having a nucleic acid sequence as set forth in SEQ ID NO: 4 for developing vaccine against SARS-CoV-2.

In an embodiment of the present disclosure, there is provided a use of a nucleic acid fragment having a nucleic acid sequence as set forth in SEQ ID NO: 5 for developing vaccine against SARS-CoV-2.

In an embodiment of the present disclosure, there is provided a use of a nucleic acid fragment having a nucleic acid sequence as set forth in any one of SEQ ID NO: 1 or 2 or 3 or 4 or 5 for developing vaccine against SARS-CoV-2.

In an embodiment of the present disclosure, there is provided a use of the oligonucleotide primer pairs as described in the present disclosure for sequencing a region of SARS-CoV-2.

In an embodiment of the present disclosure, there is provided a use of the oligonucleotide primer pairs selected from the group consisting of a nucleic acid sequence as set forth in SEQ ID NO: 6 and SEQ ID NO: 7, SEQ ID NO: 8 and SEQ ID NO: 9, SEQ ID NO: 6 and SEQ ID NO: 9, SEQ ID NO: 10 and SEQ ID NO: 11, SEQ ID NO: 12 and SEQ ID NO: 13, SEQ ID NO: 14 and SEQ ID NO: 15, SEQ ID NO: 16 and SEQ ID NO: 17, SEQ ID NO: 6 and SEQ ID NO: 13, SEQ ID NO: 6 and SEQ ID NO: 11, SEQ ID NO: 8 and SEQ ID NO: 11, SEQ ID NO: 8 and SEQ ID NO: 13, SEQ ID NO: 10 and SEQ ID NO: 13, and SEQ ID NO: 12 and SEQ ID NO: 11 for sequencing a region of SARS-CoV-2.

In an embodiment of the present disclosure, there is provided a use of the oligonucleotide primer pairs as described in the present disclosure for detecting the presence of SARS-CoV-2 in a sample.

In an embodiment of the present disclosure, there is provided a use of the oligonucleotide primer pairs selected from the group consisting of a nucleic acid sequence as set forth in SEQ ID NO: 6 and SEQ ID NO: 7, SEQ ID NO: 8 and SEQ ID NO: 9, SEQ ID NO: 6 and SEQ ID NO: 9, SEQ ID NO: 10 and SEQ ID NO: 11, SEQ ID NO: 12 and SEQ ID NO: 13, SEQ ID NO: 14 and SEQ ID NO: 15, SEQ ID NO: 16 and SEQ ID NO: 17, SEQ ID NO: 6 and SEQ ID NO: 13, SEQ ID NO: 6 and SEQ ID NO: 11, SEQ ID NO: 8 and SEQ ID NO: 11, SEQ ID NO: 8 and SEQ ID NO: 13, SEQ ID NO: 10 and SEQ ID NO: 13, and SEQ ID NO: 12 and SEQ ID NO: 11 for detecting the presence of SARS-CoV-2 in a sample.

In an embodiment of the present disclosure, there is provided a use of a nucleic acid fragment having a nucleic acid sequence with at least 95% identity to the nucleic acid sequence as set forth in any one of SEQ ID NO: 1 or 2 or 3 or 4 or 5 for drug development against SARS-CoV-2. In another embodiment, there is provided a use of a nucleic acid fragment having a nucleic acid sequence with at least 95%, or 96%, or 97%, or 98%, or 99%, or 99.5%, or 99.75%, or 99.9% identity to the nucleic acid sequence as set forth in any one of SEQ ID NO: 1 or 2 or 3 or 4 or 5 for drug development against SARS-CoV-2.

In an embodiment of the present disclosure, there is provided a use of a nucleic acid fragment having a nucleic acid sequence with at least 95%, or 96%, or 97%, or 98%, or 99%, or 99.5%, or 99.75%, or 99.9% identity to the nucleic acid sequence as set forth in SEQ ID NO: 1 for drug development against SARS-CoV-2.

In an embodiment of the present disclosure, there is provided a use of a nucleic acid fragment having a nucleic acid sequence with at least 95%, or 96%, or 97%, or 98%, or 99%, or 99.5%, or 99.75%, or 99.9% identity to the nucleic acid sequence as set forth in SEQ ID NO: 2 for drug development against SARS-CoV-2.

In an embodiment of the present disclosure, there is provided a use of a nucleic acid fragment having a nucleic acid sequence with at least 95%, or 96%, or 97%, or 98%, or 99%, or 99.5%, or 99.75%, or 99.9% identity to the nucleic acid sequence as set forth in SEQ ID NO: 3 for drug development against SARS-CoV-2.

In an embodiment of the present disclosure, there is provided a use of a nucleic acid fragment having a nucleic acid sequence with at least 95%, or 96%, or 97%, or 98%, or 99%, or 99.5%, or 99.75%, or 99.9% identity to the nucleic acid sequence as set forth in SEQ ID NO: 4 for drug development against SARS-CoV-2.

In an embodiment of the present disclosure, there is provided a use of a nucleic acid fragment having a nucleic acid sequence with at least 95%, or 96%, or 97%, or 98%, or 99%, or 99.5%, or 99.75%, or 99.9% identity to the nucleic acid sequence as set forth in SEQ ID NO: 5 for drug development against SARS-CoV-2.

In an embodiment of the present disclosure, there is provided a use of a nucleic acid fragment having a nucleic acid sequence with at least 95% identity to the nucleic acid sequence as set forth in any one of SEQ ID NO: 1 or 2 or 3 or 4 or 5 for detecting the presence of SARS-CoV-2 in a sample. In another embodiment, there is provided a use of a nucleic acid fragment having a nucleic acid sequence with at least 95%, or 96%, or 97%, or 98%, or 99%, or 99.5%, or 99.75%, or 99.99% identity to the nucleic acid sequence as set forth in any one of SEQ ID NO: 1 or 2 or 3 or 4 or 5 for detecting the presence of SARS-CoV-2 in a sample.

In an embodiment of the present disclosure, there is provided a use of a nucleic acid fragment having a nucleic acid sequence with at least 95%, or 96%, or 97%, or 98%, or 99%, or 99.5%, or 99.75%, or 99.99% identity to the nucleic acid sequence as set forth in SEQ ID NO: 1 for detecting the presence of SARS-CoV-2 in a sample.

In an embodiment of the present disclosure, there is provided a use of a nucleic acid fragment having a nucleic acid sequence with at least 95%, or 96%, or 97%, or 98%, or 99%, or 99.5%, or 99.75%, or 99.99% identity to the nucleic acid sequence as set forth in SEQ ID NO: 2 for detecting the presence of SARS-CoV-2 in a sample.

In an embodiment of the present disclosure, there is provided a use of a nucleic acid fragment having a nucleic acid sequence with at least 95%, or 96%, or 97%, or 98%, or 99%, or 99.5%, or 99.75%, or 99.99% identity to the nucleic acid sequence as set forth in SEQ ID NO: 3 for detecting the presence of SARS-CoV-2 in a sample.

In an embodiment of the present disclosure, there is provided a use of a nucleic acid fragment having a nucleic acid sequence with at least 95%, or 96%, or 97%, or 98%, or 99%, or 99.5%, or 99.75%, or 99.99% identity to the nucleic acid sequence as set forth in SEQ ID NO: 4 for detecting the presence of SARS-CoV-2 in a sample.

In an embodiment of the present disclosure, there is provided a use of a nucleic acid fragment having a nucleic acid sequence with at least 95%, or 96%, or 97%, or 98%, or 99%, or 99.5%, or 99.75%, or 99.99% identity to the nucleic acid sequence as set forth in SEQ ID NO: 5 for detecting the presence of SARS-CoV-2 in a sample.

In an embodiment of the present disclosure, there is provided a use of a nucleic acid fragment having a nucleic acid sequence as set forth in SEQ ID NO: 1 for detecting the presence of SARS-CoV-2 in a sample.

In an embodiment of the present disclosure, there is provided a use of a nucleic acid fragment having a nucleic acid sequence as set forth in SEQ ID NO: 2 for detecting the presence of SARS-CoV-2 in a sample.

In an embodiment of the present disclosure, there is provided a use of a nucleic acid fragment having a nucleic acid sequence as set forth in SEQ ID NO: 3 for detecting the presence of SARS-CoV-2 in a sample.

In an embodiment of the present disclosure, there is provided a use of a nucleic acid fragment having a nucleic acid sequence as set forth in SEQ ID NO: 4 for detecting the presence of SARS-CoV-2 in a sample.

In an embodiment of the present disclosure, there is provided a use of a nucleic acid fragment having a nucleic acid sequence as set forth in SEQ ID NO: 5 for detecting the presence of SARS-CoV-2 in a sample.

In an embodiment of the present disclosure, there is provided a nucleic acid fragment having a nucleic acid sequence with at least 95% identity to the nucleic acid sequence as set forth in any one of SEQ ID NO: 1 or 2 or 3 or 4 or 5. In another embodiment, there is provided a nucleic acid fragment having a nucleic acid sequence with at least 95%, or 96%, or 97%, or 98%, or 99%, or 99.5%, or 99.75%, or 99.99% identity to the nucleic acid sequence as set forth in any one of SEQ ID NO: 1 or 2 or 3 or 4 or 5.

In an embodiment of the present disclosure, there is provided a nucleic acid fragment having a nucleic acid sequence with at least 95%, or 96%, or 97%, or 98%, or 99%, or 99.5%, or 99.75%, or 99.99% identity to the nucleic acid sequence as set forth in any one of SEQ ID NO: 1 or 2 or 3 or 4 or 5.

In an embodiment of the present disclosure, there is provided a nucleic acid fragment having a nucleic acid sequence with at least 95%, or 96%, or 97%, or 98%, or 99%, or 99.5%, or 99.75%, or 99.99% identity to the nucleic acid sequence as set forth in SEQ ID NO: 1.

In an embodiment of the present disclosure, there is provided a nucleic acid fragment having a nucleic acid sequence with at least 95%, or 96%, or 97%, or 98%, or 99%, or 99.5%, or 99.75%, or 99.99% identity to the nucleic acid sequence as set forth in SEQ ID NO: 2.

In an embodiment of the present disclosure, there is provided a nucleic acid fragment having a nucleic acid sequence with at least 95%, or 96%, or 97%, or 98%, or 99%, or 99.5%, or 99.75%, or 99.99% identity to the nucleic acid sequence as set forth in SEQ ID NO: 3.

In an embodiment of the present disclosure, there is provided a nucleic acid fragment having a nucleic acid sequence with at least 95%, or 96%, or 97%, or 98%, or 99%, or 99.5%, or 99.75%, or 99.99% identity to the nucleic acid sequence as set forth in SEQ ID NO: 4.

In an embodiment of the present disclosure, there is provided a nucleic acid fragment having a nucleic acid sequence with at least 95%, or 96%, or 97%, or 98%, or 99%, or 99.5%, or 99.75%, or 99.99% identity to the nucleic acid sequence as set forth in SEQ ID NO: 5.

In an embodiment of the present disclosure, there is provided a nucleic acid fragment having a nucleic acid sequence as set forth in SEQ ID NO: 1.

In an embodiment of the present disclosure, there is provided a nucleic acid fragment having a nucleic acid sequence as set forth in SEQ ID NO: 2.

In an embodiment of the present disclosure, there is provided a nucleic acid fragment having a nucleic acid sequence as set forth in SEQ ID NO: 3.

In an embodiment of the present disclosure, there is provided a nucleic acid fragment having a nucleic acid sequence as set forth in SEQ ID NO: 4.

In an embodiment of the present disclosure, there is provided a nucleic acid fragment having a nucleic acid sequence as set forth in SEQ ID NO: 5.

In an embodiment of the present disclosure, there is provided at least one nucleotide fragment for the detection of COVID-19, wherein the nucleotide fragment has a nucleic acid sequence selected from the group consisting of SEQ ID NO: 18, SEQ ID NO: 19, SEQ ID NO: 20 and SEQ ID NO: 21 wherein said nucleotide fragment is used as a probe for the detection of SARS-CoV-2.

In an embodiment of the present disclosure, there is provided a kit for the detection of SARS-CoV-2, wherein the kit comprises at least one primer set selected from the group consisting of primers having a nucleic acid sequence as set forth in SEQ ID NO: 6 and SEQ ID NO: 7, primers having a nucleic acid sequence as set forth in SEQ ID NO: 8 and SEQ ID NO: 9, primers having a nucleic acid sequence as set forth in SEQ ID NO: 10 and SEQ ID NO: 11, primers having a nucleic acid sequence as set forth in SEQ ID NO: 12 and SEQ ID NO: 13, primers having a nucleic acid sequence as set forth in SEQ ID NO: 14 and SEQ ID NO: 15, and primers having a nucleic acid sequence as set forth in SEQ ID NO: 16 and SEQ ID NO: 17.

In an embodiment of the present disclosure, there is provided a kit for the detection of SARS-CoV-2, wherein the kit comprises a primer set having a nucleic acid sequence as set forth in SEQ ID NO: 6 and SEQ ID NO: 7.

In an embodiment of the present disclosure, there is provided a kit for the detection of SARS-CoV-2, wherein the kit comprises a primer set having a nucleic acid sequence as set forth in SEQ ID NO: 8 and SEQ ID NO: 9.

In an embodiment of the present disclosure, there is provided a kit for the detection of SARS-CoV-2, wherein the kit comprises a primer set having a nucleic acid sequence as set forth in SEQ ID NO: 10 and SEQ ID NO: 11.

In an embodiment of the present disclosure, there is provided a kit for the detection of SARS-CoV-2, wherein the kit comprises a primer set having a nucleic acid sequence as set forth in SEQ ID NO: 12 and SEQ ID NO: 13.

In an embodiment of the present disclosure, there is provided a kit for the detection of SARS-CoV-2, wherein the kit comprises a primer set having a nucleic acid sequence as set forth in SEQ ID NO: 14 and SEQ ID NO: 15.

In an embodiment of the present disclosure, there is provided a kit for the detection of SARS-CoV-2, wherein the kit comprises a primer set having a nucleic acid sequence as set forth in SEQ ID NO: 16 and SEQ ID NO: 17.

In an embodiment of the present disclosure, there is provided a kit for the detection of SARS-CoV-2, wherein the kit comprises at least one nucleotide fragment, said nucleotide fragment having a nucleic acid sequence as set forth in SEQ ID NO: 1, or SEQ ID NO: 2, or SEQ ID NO: 3, or SEQ ID NO: 4, or SEQ ID NO: 5, or SEQ ID NO: 18, or SEQ ID NO: 19, SEQ ID NO: 20, SEQ ID NO: 21

In an embodiment of the present disclosure, there is provided a biomarker for development of drug targets and therapeutics for treatment of SARS-CoV-2 infections, wherein the biomarker is at least 90% identical to a nucleic acid sequence as set forth in SEQ ID NO: 1.

In an embodiment of the present disclosure, there is provided a biomarker for development of drug targets and therapeutics for treatment of SARS-CoV-2 infections, wherein the biomarker is at least 90% identical to a nucleic acid sequence as set forth in SEQ ID NO: 2.

In an embodiment of the present disclosure, there is provided a biomarker for development of drug targets and therapeutics for treatment of SARS-CoV-2 infections, wherein the biomarker is at least 90% identical to a nucleic acid sequence as set forth in SEQ ID NO: 3.

In an embodiment of the present disclosure, there is provided a biomarker for development of drug targets and therapeutics for treatment of SARS-CoV-2 infections, wherein the biomarker is at least 90% identical to a nucleic acid sequence as set forth in SEQ ID NO: 4.

In an embodiment of the present disclosure, there is provided a biomarker for development of drug targets and therapeutics for treatment of SARS-CoV-2 infections, wherein the biomarker is at least 90% identical to a nucleic acid sequence as set forth in SEQ ID NO: 5.

In an embodiment of the present disclosure, there is provided a nucleic acid fragment for development of drug targets and therapeutics for treatment of SARS-CoV-2 infections, wherein the fragment is at least 90% identical to a nucleic acid sequence as set forth in SEQ ID NO: 18.

In an embodiment of the present disclosure, there is provided a nucleic acid fragment for development of drug targets and therapeutics for treatment of SARS-CoV-2 infections, wherein the fragment is at least 90% identical to a nucleic acid sequence as set forth in SEQ ID NO: 19.

In an embodiment of the present disclosure, there is provided a nucleic acid fragment for development of drug targets and therapeutics for treatment of SARS-CoV-2 infections, wherein the fragment is at least 90% identical to a nucleic acid sequence as set forth in SEQ ID NO: 20.

In an embodiment of the present disclosure, there is provided a nucleic acid fragment for development of drug targets and therapeutics for treatment of SARS-CoV-2 infections, wherein the fragment is at least 90% identical to a nucleic acid sequence as set forth in SEQ ID NO: 21.

In an embodiment of the present disclosure, there is provided a nucleic acid fragment having a nucleic acid sequence with at least 95% identity to the nucleic acid sequence selected from the group consisting of SEQ ID NO: 1, or 2, or 3, or 4, or 5, or 18, or 19, or 20, or 21 for use as epitopes for raising antibodies for detecting the presence of SARS-CoV-2. In another embodiment, the nucleic acid fragment is having at least 95%, or 96%, or 97%, or 98%, or 99%, or 99.5%, or 99.75%, or 99.99% identity to the nucleic acid sequence selected from the group consisting of SEQ ID NO: 1, or 2, or 3, or 4, or 5, or 18, or 19, or 20, or 21.

In an embodiment of the present disclosure, there is provided a method of detecting the presence of SARS-CoV-2 using the nucleotide fragment as disclosed herein, wherein the method is selected from the group consisting of PCR, RT-PCR. In another embodiment, the method is selected from well-known PCR based methods.

Although the subject matter has been described with reference to specific embodiments, this description is not meant to be construed in a limiting sense. Various modifications of the disclosed embodiments, as well as alternate embodiments of the subject matter, will become apparent to persons skilled in the art upon reference to the description of the subject matter. It is therefore contemplated that such modifications can be made without departing from the spirit or scope of the present subject matter as defined.

EXAMPLES

The disclosure will now be illustrated with working examples, which is intended to illustrate the working of disclosure and not intended to take restrictively to imply any limitations on the scope of the present disclosure. Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein. It is to be understood that this disclosure is not limited to particular methods, and experimental conditions described, as such methods and conditions may vary.

Example 1

Biomarkers and Primer Sets for Detection of SARS-CoV-2

The biomarkers were arrived upon by studying protein sequence of Spike (S) protein and the non-structural protein Nsp3 of SARS-CoV-2. The sequences of spike protein and Nsp3 region of SARS-CoV-2 was accessed using the Accession NC_045512 (Wu, Fan, et. al. Nature 579.7798 (2020): 265-269).

The biomarkers as disclosed in the present disclosure are SEQ ID NO: 1 (Biomarker-1), SEQ ID NO: 2 (Biomarker-2), SEQ ID NO: 3 (Biomarker-3), SEQ ID NO: 4 (Biomarker-4), SEQ ID NO: 5 (Biomarker-5).

SEQ ID NO: 1 depicts the nucleic acid sequence of Biomarker 1—TCTGGGACCAATGGTACTAAGAGG SEQ ID NO: 2 depicts the nucleic acid sequence of Biomarker 2—CACAAAAACAACAAAAGT SEQ ID NO: 3 depicts the nucleic acid sequence of Biomarker 3—GGTGATTCTTCTTCAGGT SEQ ID NO: 4 depicts the nucleic acid sequence of Biomarker 4—CAGACTAAT-TCTCCTCGGCGGGCA SEQ ID NO: 5 depicts the nucleic acid sequence of Biomarker 5—TTGGTCAACAAGACGGCAGT-GAGGACAATCAGACAACTACTATTCAAAC AAT-TGTTGAGGTTC SEQ ID NO: 6 to SEQ ID NO: 17 are directed to the primer sequences as per the present disclosure. Listed in Table 1 below.

SEQ ID NO: 6 depicts forward primer sequence of the primer set APAP 1. ATACATGTCTCTGGGAC-CAATGG SEQ ID NO: 7 depicts reverse primer sequence of the primer set APAP 1. ACTTTTGTTGTTTTGTGGTAATAAACAC SEQ ID NO: 8 depicts forward primer sequence of the primer set APAP 2. GACTCCTGGTGAT-TCTTCTTCAGG SEQ ID NO: 9 depicts reverse primer sequence of the primer set APAP 2. ACAGTGAAGGATTT-CAACGTACAC SEQ ID NO: 10 depicts forward primer sequence of the primer set APAP 3. GACTCAGACTAAT-TCTCCTCGG SEQ ID NO: 11 depicts reverse primer sequence of the primer set APAP 3. GACACTGGTAGAAT-TTCTGTGG SEQ ID NO: 12 depicts forward primer sequence of the primer set APAP 4. TCAGACTAATTCTCCTCGGC SEQ ID NO: 13 depicts reverse primer sequence of the primer set APAP 4. ATTTGTGGGTATGGCAATAGAG SEQ ID NO: 14 depicts forward primer sequence of the primer set APAP 5. CACTTCTGCTGCTCTTCAAC SEQ ID NO: 15 depicts reverse primer sequence of the primer set APAP 5. GCTTCTTCCACAATGTCTGC SEQ ID NO: 16 depicts forward primer sequence of the primer set APAP 6. CTTCTGCTGCTCTTCAACC SEQ ID NO: 17 depicts reverse primer sequence of the primer set APAP 6. TCTGATTGTCCTCACTGCC The Probes as Disclosed in the Present Disclosure are Depicted in SEQ ID NO: 18 to 21. Listed in Table 1 Below.

SEQ ID No: 18 depicts the probe for the oligonucleotide primer pairs APAP 3 and APAP 4. AGTCAATCCAT-CATTGCCTACACTATGTCACTT SEQ ID No: 19 depicts the probe for the oligonucleotide primer pair APAP 5. ACGGCAGTGAGGACAATCA-GACAACTACTA SEQ ID No: 20 depicts the probe for the oligonucleotide primer pair APAP 1. GAAGTCTAACAT-AATAAGAGGCTGG SEQ ID No: 21 depicts the probe for the oligonucleotide primer pair APAP 2. AGATGCTGTA-GACTGTGCACTTGAC The SEQ IDs of the Amplicons Obtained by Performing PCR Using the Oligonucleotide Primer Pair as Disclosed in the Present Disclosure APAP 1, APAP 2, APAP 3, APAP 4, APAP 5, and APAP 6.

SEQ ID NO: 22 depicts the nucleic acid sequence of the amplicon as obtained by performing PCR using the oligonucleotide primer pair APAP 1.

```
ATACATGTCTCTGGGACCAATGGTACTAAG

AGGTTTGATAACCCTGTCCTACCATTTAAT

GATGGTGTTTATTTTGCTTCCACTGAGAAG

TCTAACATAATAAGAGGCTGGATTTTTGGT

ACTACTTTAGATTCGAAGACCCAGTCCCTA

CTTATTGTTAATAACGCTACTAATGTTGTT

ATTAAAGTCTGTGAATTTCAATTTTGTAAT

GATCCATTTTGGGTGTTTATTACCACAAA

AACAACAAAAGT
```

SEQ ID NO: 23 depicts the nucleic acid sequence of the amplicon as obtained by performing PCR using the oligonucleotide primer pair APAP 2.

```
GACTCCTGGTGATTCTTCTTCAGGTTGGAC

AGCTGGTGCTGCAGCTTATTATGTGGGTTA

TCTTCAACCTAGGACTTTTCTATTAAAATA

TAATGAAAATGGAACCATTACAGATGCTGT

AGACTGTGCACTTGACCCTCTCTCAGAAAC

AAAGTGTACGTTGAAATCCTTCACTGT
```

SEQ ID NO: 24 depicts the nucleic acid sequence of the amplicon as obtained by performing PCR using the oligonucleotide primer pair APAP 3.

```
GACTCAGACTAATTCTCCTCGGCGGGCACG

TAGTGTAGCTAGTCAATCCATCATTGCCTA

CACTATGTCACTTGGTGCAGAAAATTCAGT

TGCTTACTCTAATAACTCTATTGCCATACC

CACAAATTTTACTATTAGTGTTACCACAGA

AATTCTACCAGTGTC
```

SEQ ID NO: 25 depicts the nucleic acid sequence of the amplicon as obtained by performing PCR using the oligonucleotide primer pair APAP 4.

```
TCAGACTAATTCTCCTCGGCGGGCACGTAG

TGTAGCTAGTCAATCCATCATTGCCTACAC

TATGTCACTTGGTGCAGAAAATTCAGTTGC

TTACTCTAATAACTCTATTGCCATACCCAC

AAAT
```

SEQ ID NO: 26 depicts the nucleic acid sequence of the amplicon as obtained by performing PCR using the oligonucleotide primer pair APAP 5.

```
CACTTCTGCTGCTCTTCAACCTGAAGAAGA

GCAAGAAGAAGATTGGTTAGATGATGATAG

TCAACAAACTGTTGGTCAACAAGACGGCAG

TGAGGACAATCAGACAACTACTATTCAAAC

AATTGTTGAGGTTCAACCTCAATTAGAGAT

GGAACTTACACCAGTTGTTCAGACTATTGA

AGTGAATAGTTTTAGTGGTTATTTAAAACT

TACTGACAATGTATACATTAAAAATGCAGA

CATTGTGGAAGAAGC
```

SEQ ID NO: 27 depicts the nucleic acid sequence of the amplicon as obtained by performing PCR using the oligonucleotide primer pair APAP 6.

```
CTTCTGCTGCTCTTCAACCTGAAGAAGAGC

AAGAAGAAGATTGGTTAGATGATGATAGTC

AACAAACTGTTGGTCAACAAGACGGCAGTG

AGGACAATCAGA
```

TABLE 1

Summary of the sequences as per the present disclosure

| SEQ ID NO | Type of Sequence | Genomic end position (as per the Accession NC_045512 - Wu, Fan, et al. Nature 579.7798 (2020): 265-269.) | Genomic end position (as per the Accession NC_045512 - Wu, Fan, et al. Nature 579.7798 (2020): 265-269.) | Name of Primer sets used |
|---|---|---|---|---|
| 1 | Biomarker 1 | 21773 | 21796 | |
| 2 | Biomarker 2 | 21998 | 22015 | |
| 3 | Biomarker 3 | 22316 | 22333 | |
| 4 | Biomarker 4 | 23591 | 23614 | |
| 5 | Biomarker 5 | 3228 | 3290 | |
| 6 | Primer-F | 21764 | 21786 | APAP1 |
| 7 | Primer-R | 22015 | 21987 | |
| 8 | Primer-F | 22309 | 22332 | APAP2 |
| 9 | Primer-R | 22485 | 22462 | |
| 10 | Primer-F | 23587 | 23608 | APAP3 |
| 11 | Primer-R | 23751 | 23730 | |
| 12 | Primer-F | 23590 | 23609 | APAP4 |
| 13 | Primer-R | 23713 | 23692 | |
| 14 | Primer-F | 3157 | 3176 | APAP5 |
| 15 | Primer-R | 3411 | 3392 | |
| 16 | Primer-F | 3159 | 3177 | APAP6 |
| 17 | Primer-R | 3260 | 3242 | |
| 18 | Probe for Biomarker 4 | 23627 | 23659 | APAP3 or APAP4 |
| 19 | Probe for Biomarker 5 | 3240 | 3269 | APAP5 |
| 20 | Probe for Biomarker 1 & 2 | 21850 | 21874 | APAP1 |
| 21 | Probe for Biomarker 3 | 22419 | 22444 | APAP2 |
| 22 | Amplicon obtained by using the primer pair APAP 1 (252 bp) | 21764 | 22015 | APAP 1 |
| 23 | Amplicon obtained by using the primer pair APAP 2 (177 bp) | 22309 | 22485 | APAP 2 |
| 24 | Amplicon obtained by using the primer pair APAP 3 (165 bp) | 23587 | 23751 | APAP 3 |
| 25 | Amplicon obtained by using the primer pair APAP 4 (124 bp) | 23590 | 23713 | APAP 4 |
| 26 | Amplicon obtained by using the primer pair APAP 5 (255 bp) | 3157 | 3411 | APAP 5 |
| 27 | Amplicon obtained by using the primer pair APAP 6 (102 bp) | 3159 | 3260 | APAP 6 |

Example 2

Primers for the Detection of SARS-CoV-2

Based on the biomarkers disclosed in the Example 1, six sets of oligonucleotide primers were synthesized. Table 2 below provides the sequences of the six sets of primers along with the respective melting temperature.

TABLE 2

Primer sets as disclosed in the present disclosure

| Primer set | SEQ ID NO. | Melting Temp. (Tm, °C.) | Detection of COVID-19 genome | Off targets |
|---|---|---|---|---|
| APAP 1 | SEQ ID NO. 6: Forward Primer | 59.86 | + | − |
| | SEQ ID NO. 7: Reverse Primer | 59.04 | | |
| APAP 2 | SEQ ID NO. 8: Forward Primer | 60.62 | + | − |
| | SEQ ID NO. 9: Reverse Primer | 59.49 | | |
| APAP 3 | SEQ ID NO. 10: Forward Primer | 50.0 | + | − |
| | SEQ ID NO. 11: Reverse Primer | 45.45 | | |
| APAP 4 | SEQ ID NO. 12: Forward Primer | 57.3 | + | − |
| | SEQ ID NO. 13: Reverse Primer | 56.5 | | |
| APAP 5 | SEQ ID NO. 14: Forward Primer | 57.3 | + | − |
| | SEQ ID NO. 15: Reverse Primer | 57.3 | | |

TABLE 2-continued

Primer sets as disclosed in the present disclosure

| Primer set | SEQ ID NO. | Melting Temp. (Tm, ° C.) | Detection of COVID-19 genome | Off targets |
|---|---|---|---|---|
| APAP 6 | SEQ ID NO. 16: Forward Primer | 56.7 | + | − |
|  | SEQ ID NO. 17: Reverse Primer | 56.7 |  |  |

Tagged probe for APAP 3 and APAP 4—Fluorophore 5' AGTCAATCCATCATTGCCTACACTATGTCACTT 3' Quencher (SEQ ID NO: 18).

Tagged probe for APAP 5 Fluorophore 5'ACGGCAGTGAGGACAATCAGACAACTACTA3' Quencher (SEQ ID NO: 19).

Tagged probe for APAP 1 Fluorophore 5' GAAGTCTAACATAATAAGAGGCTGG 3' Quencher (SEQ ID NO: 20).

Tagged probe for APAP 2 Fluorophore 5' AGATGCTGTAGACTGTGCACTTGAC 3' Quencher (SEQ ID NO: 21).

The primer set APAP 1 is specific for SEQ ID NO: 1 and 2, APAP 2 is specific for SEQ ID NO:3, APAP 3 and APAP 4 is specific for biomarker-4 (SEQ ID NO: 4), and the primer sets APAP 5 and APAP 6 are specific for biomarker-5 (SEQ ID NO: 5). SEQ ID NO: 1 to 5 depict the biomarkers 1-5, respectively. SEQ ID NO: 6-17 depict the primer sequence of primer sets APAP 1 to APAP 6, respectively. SEQ ID NO: 18, 19, 20 and 21 are probes for biomarkers as per the present disclosure.

However, it can be contemplated that depending upon the location of the biomarkers in the genome of SARS-CoV-2, other possible oligonucleotide primer pair combinations can also be used for detecting the presence of the virus. Some of the possible combinations are the oligonucleotide primer pairs represented by SEQ ID NO: 6 and SEQ ID NO: 13, SEQ ID NO: 6 and SEQ ID NO: 11, SEQ ID NO: 8 and SEQ ID NO: 11, SEQ ID NO: 8 and SEQ ID NO: 13, SEQ ID NO: 10 and SEQ ID NO: 13, and SEQ ID NO: 12 and SEQ ID NO: 11. Further, since the present disclosure discloses the biomarkers and the location of the same in detecting the virus, any other primers not disclosed in the present disclosure can also be used for detecting the presence of SARS-CoV-2.

Combinations of Oligonucleotide Primer Pair and the Biomarkers for Detecting the Presence of SARS-CoV-2

Figure 1:
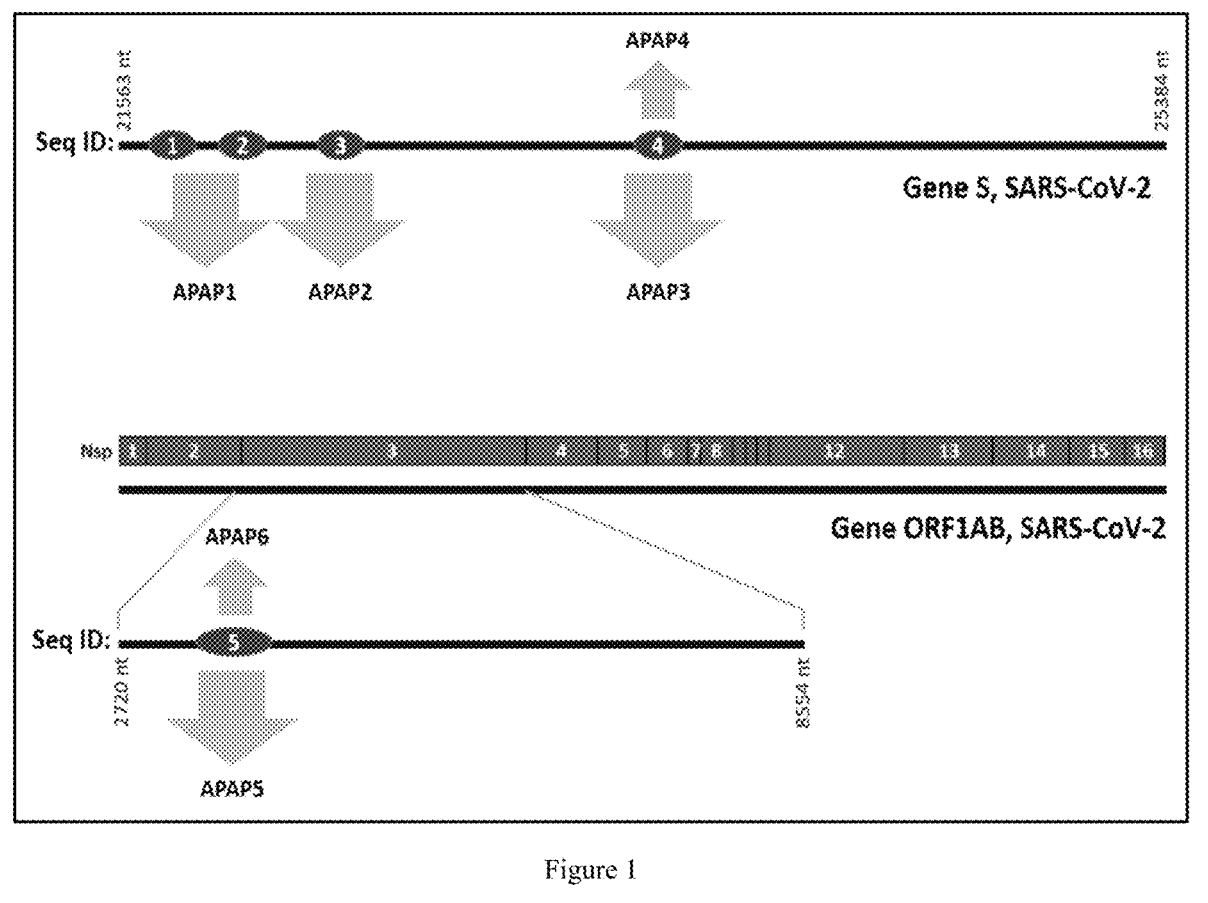

FIG. 1 depicts a schematic of the biomarkers (SEQ ID NO: 1 to 5), and the primer pairs APAP-1 (SEQ ID NO: 6 and 7), APAP-2 (SEQ ID NO: 8 and 9), APAP-3 (SEQ ID NO: 10 and 11), APAP-4 (SEQ ID NO: 12 and 13), and APAP-5 (SEQ ID NO: 14 and 15), and APAP-6 (SEQ ID NO: 16 and 17).

The present disclosure discloses five biomarkers (SEQ ID NO: 1 to 5) that would assist in detecting the presence of SARS-CoV-2. Referring to FIG. 1, the following combinations of oligonucleotide primer pair and the biomarkers can be used for the detection of the presence of SARS-CoV-2.

Biomarker-1 having a nucleic acid sequence as set forth in SEQ ID NO: 1 is detected by using the oligonucleotide primer pair of APAP-1 represented by SEQ ID NO: 6 (Forward Primer) and SEQ ID NO: 7 (Reverse Primer).

Biomarker-2 having a nucleic acid sequence as set forth in SEQ ID NO: 2 is detected by using the oligonucleotide primer pair of APAP-1 represented by SEQ ID NO: 6 (Forward Primer) and SEQ ID NO: 7 (Reverse Primer).

Biomarker-3 having a nucleic acid sequence as set forth in SEQ ID NO: 3 is detected by using the oligonucleotide primer pair of APAP-2 represented by SEQ ID NO: 8 (Forward Primer) and SEQ ID NO: 9 (Reverse Primer).

Biomarker-4 having a nucleic acid sequence as set forth in SEQ ID NO: 4 is detected by using the oligonucleotide primer pair of APAP-3 represented by SEQ ID NO: 10 (Forward Primer) and SEQ ID NO: 11 (Reverse Primer). The Biomarker-4 can also be detected by the oligonucleotide primer pair of APAP-4 represented by SEQ ID NO: 12 (Forward Primer) and SEQ ID NO: 13 (Reverse Primer).

Biomarker-5 having a nucleic acid sequence as set forth in SEQ ID NO: 5 is detected by using the oligonucleotide primer pair of APAP-5 represented by SEQ ID NO: 14 (Forward Primer) and SEQ ID NO: 15 (Reverse Primer). The Biomarker-5 can also be detected by the oligonucleotide primer pair of APAP-6 represented by SEQ ID NO: 16 (Forward Primer) and SEQ ID NO: 17 (Reverse Primer).

Example 3

Method of Detecting SARS-CoV-2

PCR Based Method:

One-Step Reverse Transcription Real-Time-PCR

One-step SYBR Green or fluorescent probe-based based Reverse Transcription real-time-PCR is performed using the following controls: NTC: No Template control; PTC: Positive control (synthetic viral RNA fragments); and HSC: Human RNA control (monitors specificity—negative control).

For SYBR Green based method ("probe-free") or fluorescent probe-based chemistry, reactions are set up using respective commercially procured one-step real-time RT-PCR master mixes available from multiple manufacturers including, but not limited to Qiagen, Thermo Fisher Scientific and Merck KGaA. It is to be contemplated that SYBR-green, SYBR-green derivatives and other substitute fluorescent dye chemistries working based on quantitative binding to double stranded DNA can be used for the purposes of the present disclosure. Reactions are set by adding primer pairs (Forward and reverse) at a final concentration of 0.5 µM to the 2× master mix and master mix supplements. In case of probe-based detection, probes are added to the reaction at 0.25-0.5 µM concentration. In case of SYBR green based protocol, the reaction mix is supplemented with 0.5-1 ng random hexamer primer. RNA was isolated from patient samples using well-known methodologies. The RNA samples are added to the reaction mix at a volume of 4-5 µL and the volume made up to 20 µL in 96 well thin wall PCR plates or equivalent reaction tubes (0.1-0.2 mL) matching the RT-PCR equipment. The samples were subjected to PCR and data acquisition in a real time PCR equipment following the cycling conditions below.

Reverse transcription and real-time cycling profile is given in Table 3 below:

TABLE 3

Reaction cycle

|  | Temperature | Time | Cycles |
|---|---|---|---|
| Reverse transcription | 50° C. | 20 min | 1 |
| RT inactivation/ initial denaturation | 95° C. | 2 min | 1 |
| Denature | 95° C. | 10 sec | 1 |
| Anneal/extend | 60° C. | 20 sec | 35-45 |

In case of SYBR-Green based assay, additional melt-analysis is performed from 60° C. to 95° C. or as suggested by the equipment manufacturer. The data is interpreted based on positive and negative control wells/tubes. In case of probe-free chemistry, the melting temperature (Tm) is used to monitor the specificity of the amplified products.

The PCR methods as described in the present example was followed for all the controls taken for the study. 2× RT-PCR buffer as used herein comprises buffer, SYBR Green dye, dNTPs and DNA polymerase. Several custom formulations are available commercially.

The temperatures of reaction steps while performing the PCR will vary depending upon the primer used. The melting temperatures of six of the primer sets which are disclosed in the present disclosure are described in Table 2.

It is to be noted here that the protocol as disclosed in the present disclosure is optimized for one-step RT-PCR which allows conversion of RNA to cDNA and amplification of the cDNA by PCR in the same tube. A possible variation is two-step RT-PCR in which cDNA synthesis and PCR are done separately. Other variations in the buffer components, use of different polymerases, use of different reaction chemistry, iterations to the primer concentration, and template concentration are well within the understanding of a person skilled in the art and is intended to be covered in the present disclosure.

Example 4

PCR Based Method Using APAP 1 Oligonucleotide Primer Pair (SEQ ID NO: 6 and SEQ ID NO: 7) for Detection of Biomarkers 1 (SEQ ID NO: 1) and 2 (SEQ ID NO: 2)

Figure 2:
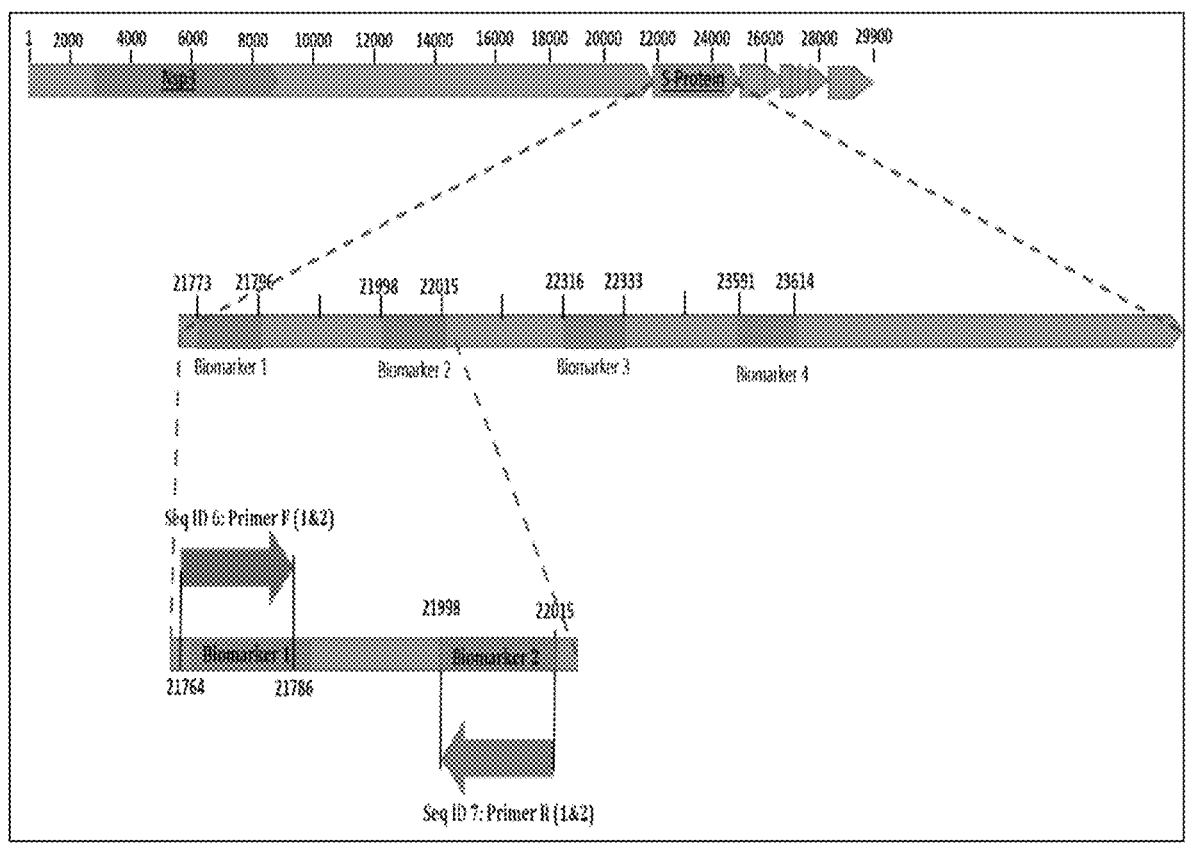
FIG. 2 depicts a schematic representation of COVID-19 virus genome portion depicting coding stretch for the S-Protein. The genomic positions of Biomarkers 1 and 2 and the forward (SEQ ID NO: 6) and reverse (SEQ ID NO: 7) primer sequence for amplification of these Biomarkers are shown, in accordance with an embodiment of the present disclosure.

FIG. 2 depicts the schematic of Biomarker 1 and Biomarker 2, and binding of the oligonucleotide primer pair (SEQ ID NO: 6 and 7) for detecting the presence of SARS-CoV-2.

RNA was extracted from a sample which ought to be tested for the presence of SARS-CoV-2. RNA extraction was done using phenol-chloroform based commercial RNA isolation reagents (e.g. Trizol from Thermo Fisher Scientific). The commercial solution can be directly added to samples and RNA isolated by phase—separation followed by precipitation. The sample used in the present example was a nasopharyngeal swab of a patient. However, RNA extracted from other samples like sputum, blood, lung biopsy, pleural fluid, and tracheal aspirate can be used for detecting the presence of SARS-CoV-2. Further, the possibility of using any such samples from patients is intended to be a part of the present disclosure.

Probe-Free Method

One-step SYBR Green or fluorescent dye-based based Reverse Transcription real-time-PCR was performed using the following controls:
  NTC: No Template control
  PC: Positive control (synthetic viral RNA fragments)
  HSC: Human RNA control (monitors specificity—negative control)

Reactions were set up using one-step real-time RT-PCR master mix from Qiagen. Reactions were set by adding the required primer pairs (for this example, SEQ ID NO: 6 and 7) at a final concentration of 0.5 µM to the 2× master mix and master mix supplements and reverse transcriptase enzyme. The reaction mix was supplemented with 0.5 ng random hexamer primer. PC RNA, NTC or HSC were added to the reaction mix at 4 µL and the volume made up to 20 µL in 96 well thin wall PCR. The samples were subjected to PCR and data acquisition in a real time PCR equipment following the cycling conditions below in table 4. The sample were first subjected to reverse transcription followed by the amplification of the target sequence.

For the purposes of the present disclosure, SYBR Green was used as a fluorescent dye for detecting the presence of the amplicon produced by the primer pair. However, it is well understood that any well-known fluorescent dye can be used instead of SYBR Green for the purposes of detection of SARS-CoV-2 as per the present disclosure. Some of the possible fluorescent dyes that can be used for the purposes of the present disclosure not limiting to EvaGreen, SYTO-13, SYTO-16, SYTO-80, SYTO-82, BEBO are disclosed herewith.

TABLE 4

Reverse transcription and real-time cycling profile

|  | Temperature | Time | Cycles |
|---|---|---|---|
| Reverse transcription | 50° C. | 20 min | 1 |
| RT inactivation/ initial denaturation | 95° C. | 2 Min | 1 |
| Denature | 95° C. | 10 Sec | 1 |
| Anneal/extend | 60° C. | 20 Sec | 40 |
| Melt analysis | 60-95° C. analysis |  | 1 |

Table 5 below provides the data generated with the oligonucleotide primer pair of APAP-1 (SEQ ID NO: 6 and 7). It can be observed from Table 7, that the primer pair APAP-1 is able to effectively detect the presence of SARS-CoV-2 in the sample by detecting the presence of Biomarkers 1 and 2. Also, the detection using the present primer set is sensitive owing to the ability of the reaction to pick up even 20 copy numbers of the viral nucleic acid material per reaction.

TABLE 5

|  | APAP1 Assay | | Specific band on |
|---|---|---|---|
| Samples | Average Ct value | Tm (° C.) | gel (Amplicon of 251 bp) |
| 20000 copies | 23.13 | 77.90 | Present |
| 2000 copies | 27.85 | 77.88 | Present |
| 200 copies | 32.00 | 77.88 | Present |
| 20 copies | 34.78 | 78.35 | Present |
| water | 36.72 | 71.65 | Absent |

Probe-Based Method

FIG. 3 depicts the schematic of the oligonucleotide primer pair APAP-1 (SEQ ID NO: 6 and 7) for detecting the presence of SARS-CoV-2 in the presence of a probe having a nucleic acid sequence as set forth in SEQ ID NO: 20. Although specific nucleic acid sequence of the probes to be used with the respective primer pairs have been disclosed in the present disclosure, however, any probe having a fluorophore and a quencher linked to the probe, wherein the probe comprises a nucleic acid sequence of at least 20 nucleotides in length, and having at least 90% identity to the nucleic acid sequence as set forth in any one of SEQ ID NO: 1 or SEQ ID NO: 2 or SEQ ID NO: 3 or SEQ ID NO: 4 or SEQ ID NO: 5 can be used for the purposes of the present disclosure.

One-step fluorescent probe-based based Reverse Transcription real-time-PCR was performed using the following controls: NTC: No Template control, PTC: Positive control (synthetic viral RNA fragments), HSC: Human RNA control (monitors specificity—negative control). The reactions were set up using commercially procured one-step fluorescent probe-based real-time RT-PCR master mixes available from multiple manufacturers including, but not limited to Qiagen, Thermo Fisher Scientific and Merck KGaA. Reactions were set by adding the respective primer pairs (for this example, SEQ ID NO: 6 and SEQ ID NO: 7) at a final concentration of 0.5 µM to the 2× master mix and master mix supplements. Probe was added to the reaction at 0.25-0.5 µM concentration. RNA isolated from patient samples were added to the reaction mix at 4-5 µL and the volume made up to 20 µL in 96 well thin wall PCR plates or equivalent reaction tubes (0.1-0.2 mL) matching the RT-PCR equipment. For the purposes of the present disclosure, TaqMan based probe chemistry was used in which FAM was used as a fluorophore, and BHQ1 was used as a quencher. However, it is to be understood that any known combination of fluorophore and quencher can be used and attached to the probe as disclosed in the present disclosure for the purposes of detecting the presence of SARS-CoV-2. Also, other probe chemistry like BHQNova probe and Light Cycler Hybridization Probe can be used for the purposes of the present disclosure.

A non-limiting list of fluorophore and quencher combinations that can be used for the probe-based PCR detection method as disclosed herein is FAM-BHQ0, HEX-BHQ1, CY5-BHQ3, FAM-TAMRA, TET-TAMRA.

Apart from the mentioned combinations of fluorophore and quencher, other combinations that can be used are: Alexa 350-Dabcyl, Pacific Blue-Dabcyl, Marina Blue-Dabcyl, Acridine-Dabcyl, Edans-Dabcyl, Coumarin-Dabcyl, BODIPY 493/513-Dabcyl, Cy2-Dabcyl, BODIPY FL-X-Dabcyl, DANSYL-Dabcyl, Alexa 488-BHQ1, FAM-BHQ1, Oregon Green-BHQ1, Rhodamine Green X-BHQ1, NBD X-BHQ1, TET-BHQ1, Alexa-430-BHQ1, BODIPY R6GX-BHQ1, Joe-BHQ1, Yakima Yellow-BHQ1, Alexa 532-BHQ1, VIC-BHQ1, HEX-BHQ1, R6G-BHQ2, Alexa 555-BHQ2, BODIPY 564/570-BHQ2, BODIPY TMR-X-BHQ2, Cy3-BHQ2, Alexa 546-BHQ2, TAMRA-BHQ2, Rhodamine Red X-BHQ2, BODIPY 581/591-BHQ2, Redmond Red-BHQ2, Cy3.5-BHQ2, ROX-BHQ2, Alexa 568-BHQ2, Cal Red-BHQ2, BIODIPY TR-X-BHQ2, Alexa 594-BHQ2, BIODIPY 630/650 X-BHQ2, LC Red 640-BBQ-650, Alexa 633-BBQ-650, BIODIPY 650/655 X-BBQ-650, Alexa 647-BBQ-650, Cy5-BBQ-650, Alexa 660-BBQ-650, Cy5.5-BBQ-650, Alexa 680-BBQ-650, LC Red 705-BBQ-650, Alexa 700-BBQ-650, and Alexa 750-BBQ-650. The names of the fluorophore and quencher has been mentioned in the following manner, "Fluorophore"-"Quencher" and the names used herein are well known to a person skilled in the art and can use any of the known combinations.

Table 6 below mentions the IUPAC name of a few of the fluorescent dyes, and fluorophore and quencher as described in the present disclosure.

TABLE 6

Fluorescent Dyes and their IUPAC Names

| Dye Name | IUPAC ID |
|---|---|
| SYBR Green I | N',N'-dimethyl-N-[4-[(E)-(3-methyl-1,3-benzothiazol-2-ylidene)methyl]-1-phenylquinolin-1-ium-2-yl]-N-propylpropane-1,3-diamine |
| BEBO | 4-[(3-methyl-6-(benzothiazol-2-yl)-2,3-dihydro-(benzo-1,3-thiazole)-2-methylidene) ]-1-methyl-pyridinium iodide |
| EvaGreen | (3-N,3-N,6-N,6-N-Tetramethylacridine-3,6-diamine)-N,N'-(oxydi-2,1-ethanediyl)bis-decanamide-(3-N,3-N,6-N,6-N-Tetramethylacridine-3,6-diamine) |
| 6-FAM | 6-carboxyfluorescein |
| TAMRA | 5-Carboxytetramethylrhodamine |
| 6-TET | 6-Carboxy-2',4,7',7-tetrachlorofluorescein |

The samples were subjected to PCR and data acquisition in a real time PCR equipment following the cycling conditions given in table 7 below.

TABLE 7

Reverse transcription and real-time cycling profile:

| | Temperature | Time | cycles |
|---|---|---|---|
| Reverse transcription | 50° C. | 20 min | 1 |
| RT inactivation/ initial denaturation | 95° C. | 2 Min | 1 |
| Denature | 95° C. | 10 sec | 1 |
| Anneal/extend | 60° C. | 20 Sec | 5-45 |

The data was interpreted based on the positive and negative control wells/tubes, using the Ct values obtained from the readout.

Example 5

PCR Based Method Using APAP 2 Oligonucleotide Primer Pair (SEQ ID NO: 8 and SEQ ID NO: 9) for Detecting Biomarker 3 (SEQ ID NO: 3)

Figure 4:
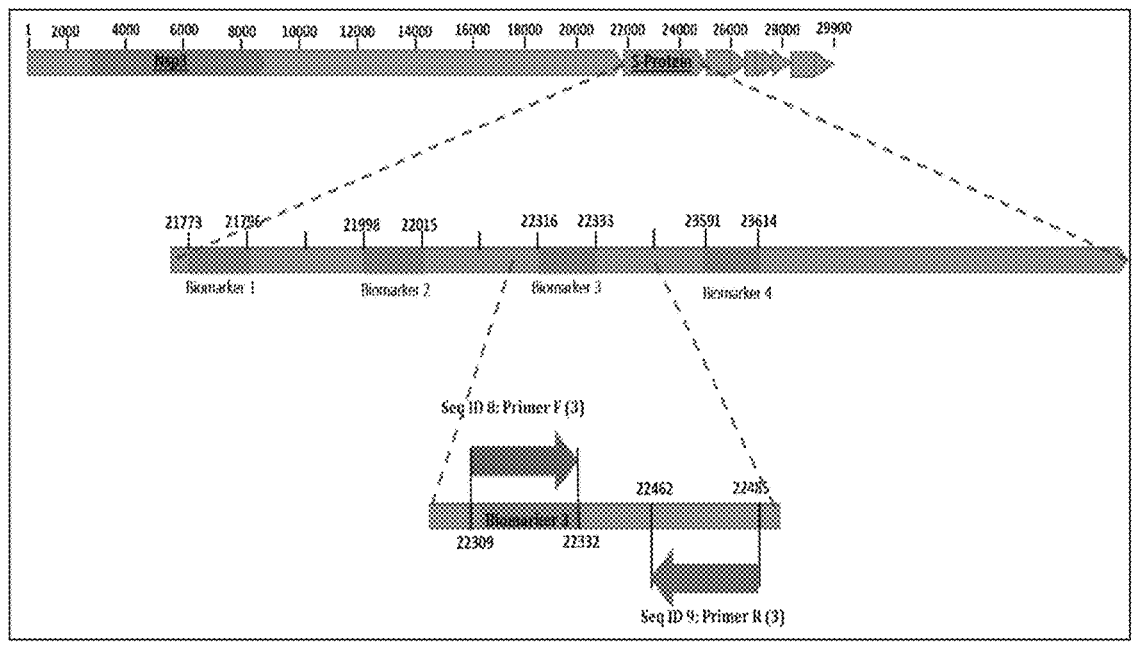

FIG. 4 depicts the schematic of Biomarker 3, and the oligonucleotide primer pair APAP 2 (SEQ ID NO: 8 and 9) used in detecting the presence of SARS-CoV-2.

RNA was extracted by known methods from a sample which ought to be tested for the presence of SARS-CoV-2.

Probe-Free Method

The method followed for the detection is the same as that described in Example 4 including the types of control to be used. The oligonucleotide primer pair used is APAP 2 represented by SEQ ID NO: 8 and SEQ ID NO: 9. Table 8 below provides the data generated with the oligonucleotide primer pair of APAP-2 (SEQ ID NO: 8 and 9).

Table 8 describes the average Ct values and melting temperatures for samples with different copy numbers. It can be observed that the primer pair APAP-2 is able to efficiently detect the presence of SARS-CoV-2 by detecting the Biomarker-3. Further, the method as described herein is highly sensitive because the primer pair APAP-2 is able to pick up even 20 copies of the viral nucleic acid material per reaction.

TABLE 8

| Samples | APAP2 Assay | | Specific band on gel (Amplicon of 176 bp) |
|---|---|---|---|
| | Average Ct value | Tm (° C.) | |
| 20000 copies | 20.99 | 78.85 | Present |
| 2000 copies | 25.61 | 78.85 | Present |
| 200 copies | 27.23 | 78.85 | Present |
| 20 copies | 28.00 | 78.85 | Present |
| Water | No Ct | N.A. | Absent |

Probe-Based Method

Figure 5:
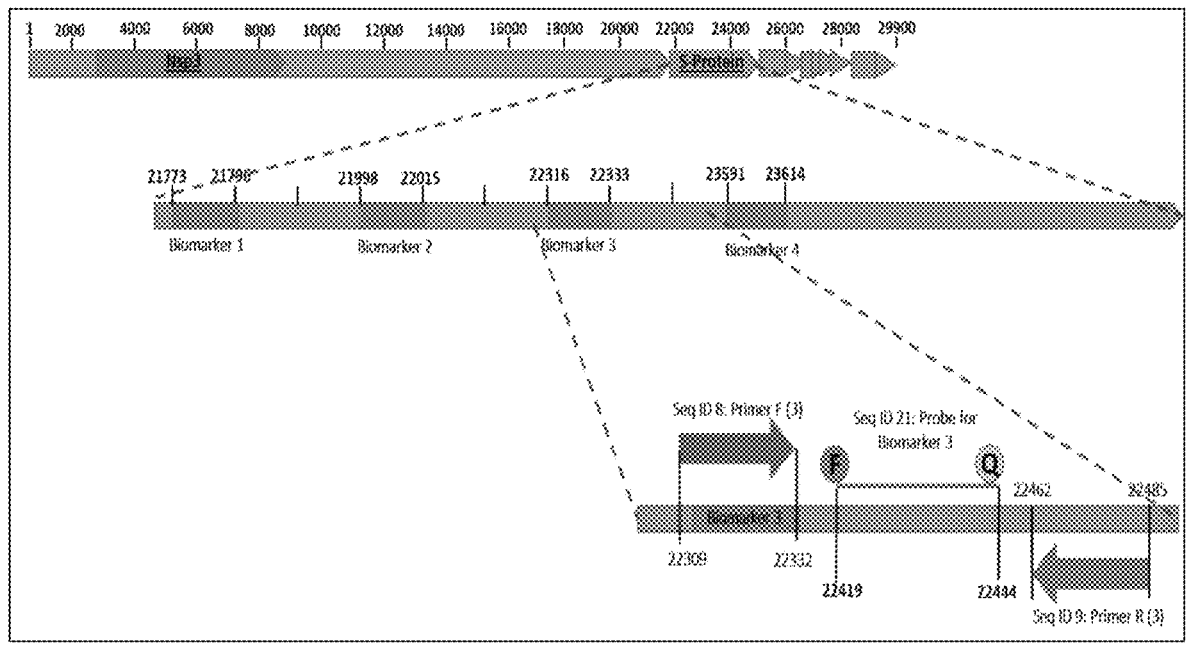

FIG. 5 depicts the schematic for the Biomarker-3, oligonucleotide primer pair APAP-2 (SEQ ID NO: 8 and 9), and probe having a nucleic acid sequence as set forth in SEQ ID NO: 21 for performing probe-based PCR detection of SARS-CoV-2.

The method followed for the detection is the same as that described in Example 4 including the types of control to be used. The probe having a nucleic acid sequence as set forth in SEQ ID NO: 21 is tagged with a fluorophore, namely FAM, and a quencher, namely, BHQ1. However, it is understood that a person skilled in the art can used any known probe chemistry and known combinations of a fluorophore and a quencher for the purpose of the present disclosure.

Example 6

PCR Based Method Using APAP 3 Oligonucleotide Primer Pair (SEQ ID NO: 10 and SEQ ID NO: 11) and APAP 4 Oligonucleotide Primer Pair (SEQ ID NO: 12 and SEQ ID NO: 13) for Detecting the Presence of Biomarker 4 (SEQ ID NO: 4)

Figure 6:
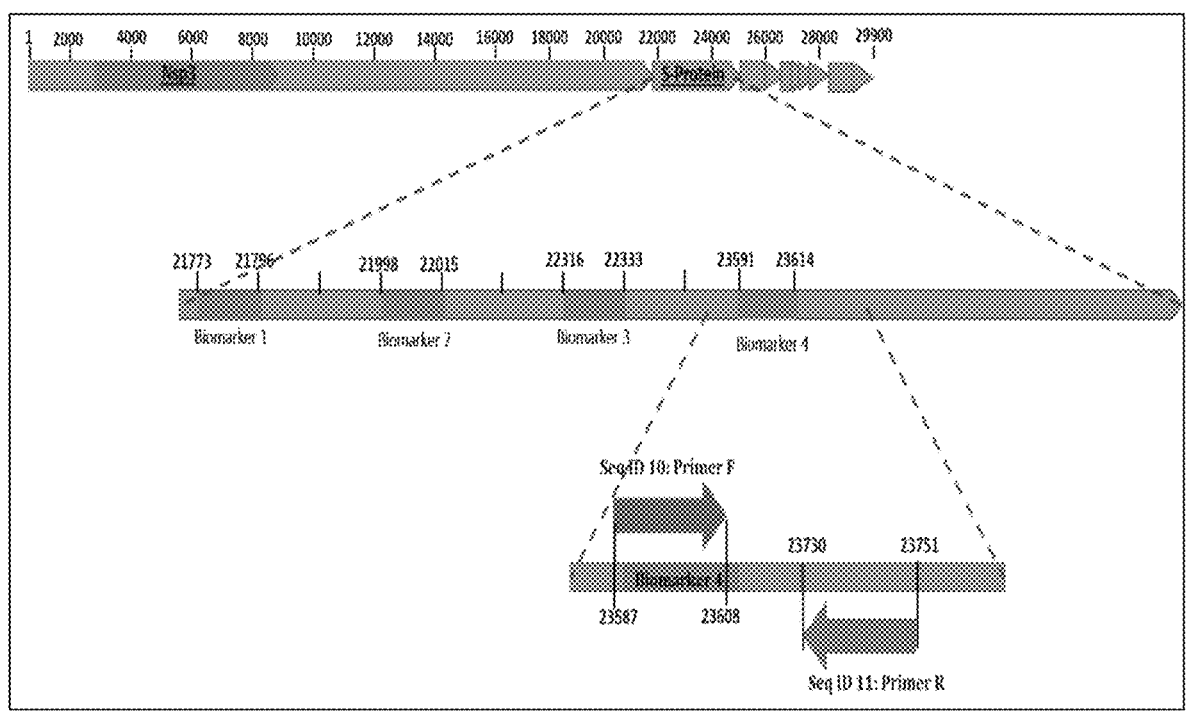

FIG. 6 depicts the schematic of Biomarker 4, and the oligonucleotide primer pair APAP 3 (SEQ ID NO: 10 and 11) used in detecting the presence of SARS-CoV-2.

RNA was extracted by known methods from a sample which ought to be tested for the presence of SARS-CoV-2.

Probe-Free Method

The method followed for the detection is the same as that described in Example 4 including the types of control to be used.

Table 9 below provides the data generated with the oligonucleotide primer pair of APAP-3, and Table 10 provides the data generated with the oligonucleotide primer pair APAP-4.

TABLE 9

| Samples | APAP3 Assay | | Specific band on gel (Amplicon of 164 bp) |
|---|---|---|---|
| | Average Ct value | Tm (° C.) | |
| 20000 copies | 21.80 | 78.90 | Present |
| 2000 copies | 25.48 | 78.90 | Present |
| 200 copies | 29.06 | 78.88 | Present |
| 20 copies | 31.30 | 78.88 | Present |
| water | 38.26 | 74.58 | Absent |

TABLE 10

| Sample | APAP4 Assay | | Specific band in gel (Amplicon of 123 bp) |
|---|---|---|---|
| | Average Ct value | Tm (° C.) | |
| 400 copies | 29.39 | 78.9 | Present |
| 40 copies | 32.58 | 78.9 | Present |
| 4 copies | 34.33 | 79.38 | Present |
| Human RNA | 35.98 | 86.81 | Absent |
| water | No Ct | N.A. | Absent |

It can be appreciated from Table 9 and 10 that both the primer pairs of APAP-3 and APAP-4 are able to effectively detect the presence of SARS-CoV-2 by detecting the presence of Biomarker 4. Further, the primer pair APAP-4 is able to pick up even 4 copies per reaction, therefore, being a highly sensitive primer pair. Also, one can observe from Table 10, that the primer pair APAP-4 is highly specific and does not provide false positive results with human RNA material. Therefore, the oligonucleotide primer pair as disclosed in the present disclosure provides sensitivity as well as specificity for detecting the presence of SARS-CoV-2.

Probe-Based Method

Figure 7:
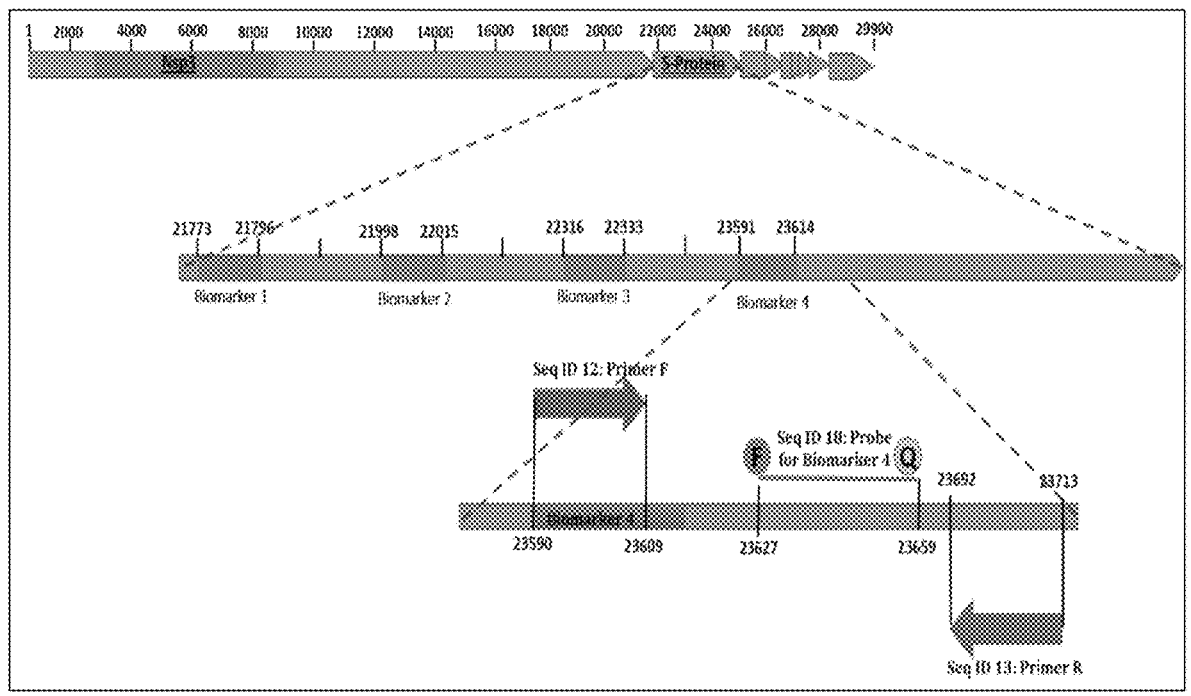

FIG. 7 depicts the schematic for the Biomarker-4, oligonucleotide primer pair APAP-4 (SEQ ID NO: 12 and 13), and probe having a nucleic acid sequence as set forth in SEQ ID NO: 18 for performing probe-based PCR detection of SARS-CoV-2.

The probe-based method followed for the detection is the same as that described in Example 4 including the types of control to be used. The probe having a nucleic acid sequence as set forth in SEQ ID NO: 18 is tagged with a fluorophore, namely FAM, and a quencher, namely, BHQ1. However, it is understood that a person skilled in the art can use any known probe chemistry and known combinations of a fluorophore and a quencher for the purpose of the present disclosure.

Example 7

PCR Based Method Using APAP 5 Oligonucleotide Primer Pair (SEQ ID NO: 14 and SEQ ID NO: 15) and APAP 6 Oligonucleotide Primer Pair (SEQ ID NO: 16 and SEQ ID NO: 17) for Detecting the Presence of Biomarker 5 (SEQ ID NO: 5)

Figure 8:
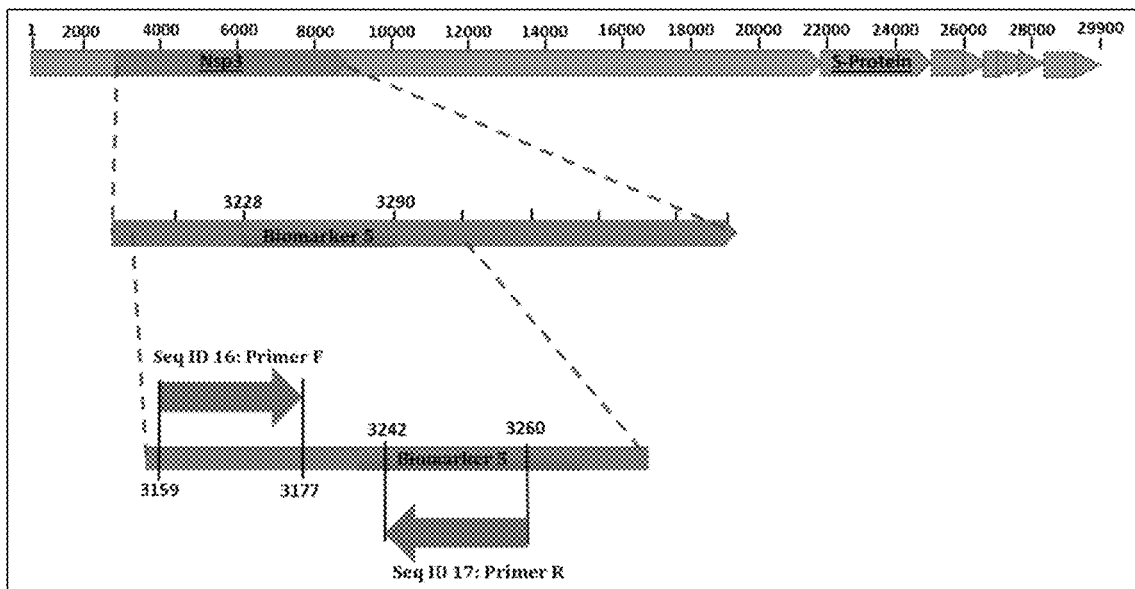

FIG. 8 depicts the schematic for the Biomarker 5, oligonucleotide primer pair APAP-6 (SEQ ID NO: 16 and 17).

RNA was extracted by known methods from a sample which ought to be tested for the presence of SARS-CoV-2.

Probe-Free Method

The method followed for the detection is the same as that described in Example 4 including the types of control to be used.

Table 11 below provides the data generated with the oligonucleotide primer pair of APAP-5.

TABLE 11

| Sample | APAP5 Assay | | Specific band on gel (Amplicon of 254 bp) |
|---|---|---|---|
| | Average Ct value | Tm (° C.) | |
| 10000 copies | 26.70 | 79.34 | Present |
| 1000 copies | 30.33 | 79.34 | Present |

TABLE 11-continued

|  | APAP5 Assay | | Specific band on |
| --- | --- | --- | --- |
| Sample | Average Ct value | Tm (° C.) | gel (Amplicon of 254 bp) |
| 100 copies | 33.56 | 79.34 | Present |
| 10 copies | 38.26 | 79.34 | Present |
| water | No Ct | N.A. | Absent |

Table 12 below provides the data generated with the oligonucleotide primer pair of APAP-6.

TABLE 12

|  | APAP6 Assay | | Specific band on |
| --- | --- | --- | --- |
| Sample | Average Ct value | Tm (° C.) | gel (Amplicon of 101 bp) |
| 10000 copies | 26.57 | 77.92 | Present |
| 1000 copies | 30.25 | 78.38 | Present |
| 100 copies | 33.45 | 78.38 | Present |
| 10 copies | 37.09 | 78.42 | Present |
| water | No Ct | N.A. | Absent |

It can be appreciated from Table 11 and Table 12 that both the oligonucleotide primer pairs of APAP-5 and APAP-6 are able to effectively detect the presence of COVID-19 by detecting the presence of Biomarker 5 in the sample. Further, high sensitivity of the primer pairs can be observed since they are able to pick up as less as 10 copies per reaction.

Probe-Based Method

Figure 9:
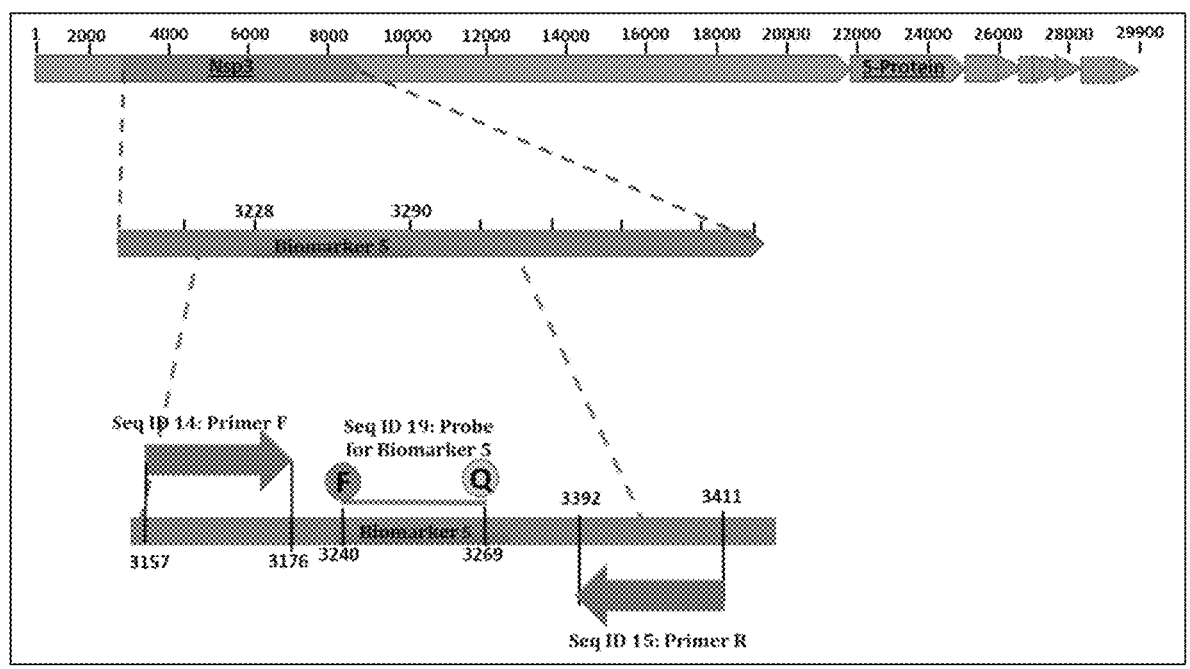

FIG. 9 depicts the schematic for the Biomarker-5, oligonucleotide primer pair APAP-5 (SEQ ID NO: 14 and 15), and probe having a nucleic acid sequence as set forth in SEQ ID NO: 19 for performing probe-based PCR detection of SARS-CoV-2.

The probe-based method followed for the detection is the same as that described in Example 4 including the types of control to be used. The probe having a nucleic acid sequence as set forth in SEQ ID NO: 19 is tagged with a fluorophore, namely FAM, and a quencher, namely, BHQ1. However, it is understood that a person skilled in the art can used any known probe chemistry and known combinations of a fluorophore and a quencher for the purpose of the present disclosure.

Summary of the Studies Performed with Oligonucleotide Primer Pairs, Biomarkers, and Probes as Disclosed in the Present Disclosure in Examples 4 to 7.

Figure 10:
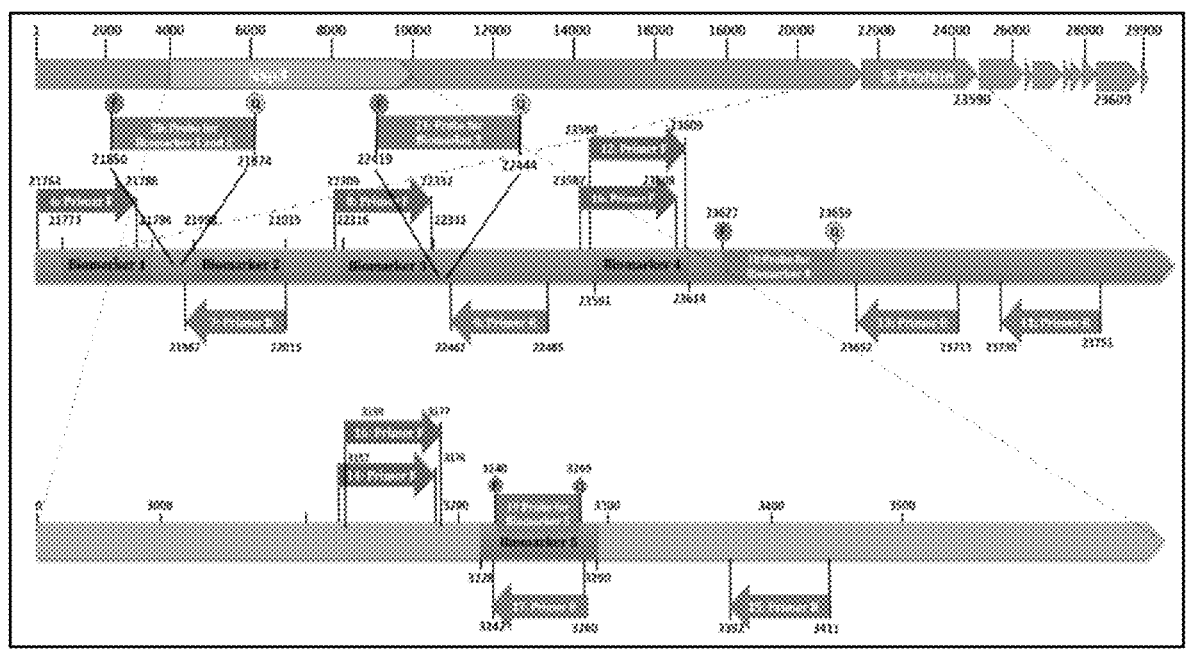

FIG. 10 depicts the complete picture of all biomarkers, primers and probes and their respective positions as disclosed in the present disclosure. Numbers represent the respective genomic position in Covid-19 genome (NC_045512) and the map depicted is not up to the scale.

FIG. 11 depicts the melting temperature of the oligonucleotide primer pair sets used in the present disclosure. Further, it can be summarised that the oligonucleotide primer pairs as disclosed herein provides for a highly sensitive and selective PCR detection method for detecting the presence of SARS-CoV-2 in a sample.

Table 13 below depicts the SEQ ID Nos for the various amplicons obtained by using the oligonucleotide primer pairs of APAP-1 to APAP-6 as disclosed in the present disclosure.

TABLE 13

| Oligonucleotide Primer Pair | Primers | Amplicon length (bp) |
| --- | --- | --- |
| APAP1 | Primer-F (SEQ ID NO: 6) Primer-R (SEQ ID NO: 7) | 251 (SEQ ID NO: 22) |
| APAP2 | Primer-F (SEQ II) NO: 8) Primer-R (SEQ ID NO: 9) | 176 (SEQ ID NO: 23) |
| APAP3 | Primer-F (SEQ ID NO: 10) Primer-R (SEQ ID NO: 11) | 164 (SEQ ID NO: 24) |
| APAP4 | Primer-F (SEQ ID NO: 12) Primer-R (SEQ ID NO: 13) | 123 (SEQ ID NO: 25) |
| APAP5 | Primer-F (SEQ ID NO: 14) Primer-R (SEQ ID NO: 15) | 254 (SEQ ID NO: 26) |
| APAP6 | Primer-F (SEQ ID NO: 16) Primer-R (SEQ ID NO: 17) | 101 (SEQ ID NO: 27) |

Bioinformatic analyses clearly show that the primers/probes designed will not be able to bind to other closely related SARS-CoV-2es including SARS-CoV-1. Human transcripts (human transcriptome) represents the largest repertoire of RNA in any human sample, posing challenges for the specificity of real-time PCR assays. At the lab-scale, RNA extracts from three human cell lines (every human cell line actively expresses greater than 20000 transcripts) were tested and no amplified products were detected in any of the cell lines. One of the assay with Primer set APAP4 was tested at Indian Council of Medical Research (ICMR) with COVID-19/SARS-CoV-2 positive samples and samples from other closely related respiratory viruses including Influenza A and B yielded results which indicated high specificity and high sensitivity to COVID-19.

It was observed that all the primer sets—APAP 1 to APAP 6 were consistently able to pick up less than 20 copies per reaction. The primer set APAP4 consistently picked up less than 10 copies per reaction, therefore, the present disclosure provides oligonucleotide primer pairs which can detect the presence of SARS-CoV-2 in a highly selective and specific manner.

The examples describing different oligonucleotide primer pair as described in the Examples 4-7 make use of only one primer pair for a single PCR reaction. However, it is well within the understanding of a person skilled in the art that more than one primer pair can be used for the detection of the virus in a method known as multiplex PCR. Multiplex PCR is a well-practised method in which more than one primer pair is used for producing more than one amplicon. Further, the multiplex PCR assays can be done by using probe-based PCR method as disclosed in the present disclosure, Although the Examples 4 to 7 describe the process using specific primer pairs APAP 1 (SEQ ID NO: 6 and SEQ ID NO: 7), APAP 2 (SEQ ID NO: 8 and SEQ ID NO: 9), APAP 3 (SEQ ID NO: 10 and SEQ ID NO: 11), APAP 4 (SEQ ID NO: 12 and SEQ ID NO: 13), APAP 5 (SEQ ID NO: 14 and SEQ ID NO: 15), and APAP 6 (SEQ ID NO: 16 and SEQ ID NO: 17), the use of other primer pairs such as SEQ ID NO: 6 and SEQ ID NO: 13, SEQ ID NO: 6 and SEQ ID NO: 11, SEQ ID NO: 8 and SEQ ID NO: 11, SEQ ID NO: 8 and SEQ ID NO: 13, SEQ ID NO: 10 and SEQ ID NO: 13, and SEQ ID NO: 12 and SEQ ID NO: 11 is contemplated to be well-within the purview of the present disclosure.

Example 8

Kits for the Detection of the Presence of SARS-CoV-2

The present example describes the kits that the present disclosure discloses comprising the oligonucleotide primer pairs.

Kit for Performing Probe-Free PCR Detection

Table 14 below describes the components of the kit for performing probe-free PCR detection. Any other component or any substitute which is well-known in the art for incorporating into kits for PCR-based detection is contemplated to be a part of the present disclosure.

TABLE 14

| Sr. No. | List of components | Description |
| --- | --- | --- |
| 1. | One step RT-PCR mix (ORP) | PCR compatible buffer, fluorescent label (SYBR Green dye), dNTPs and DNA polymerase. Several custom formulations are available commercially |
| 2. | Reverse transcriptase (RT) | Several variants available commercially |
| 3. | ROX dye | Internal reference control dye available from several sources commercially |
| 4. | Nuclease free water | Available from several sources commercially |
| 5. | COVID-19 Assay 1 primer F (COVID-19-FP) | Any one of oligonucleotide primer pair as disclosed in the present disclosure. More primers can be used for performing multiplex PCR reactions. |
| 6. | COVID-19 Assay 1 primer R (COVID-19-RP) | Any one of oligonucleotide primer pair as disclosed in the present disclosure. More primers can be used for performing multiplex PCR reactions. |
| 7. | Random-hexamer primer | Available from several sources commercially |
| 8. | GAPDH primer F | Primer sequences obtained from literature, custom synthesized |
| 9. | GAPDH primer R | Primer sequences obtained from literature, custom synthesized |
| 10. | Positive control (in-vitro transcribed RNA) (PC) | Lab-synthesized RNA which contains the regions encompassing the biomarkers as well as human GAPDH mRNA as internal control |
| 11. | No-template control (NTC) | Nuclease-free water used as RNA-free negative control |

Kit for Performing Probe-Based PCR Detection for the Presence of SARS-CoV-2

Table 15 depicts the different components of a kit for performing probe-based detection. Any other component or any substitute which is well-known in the art for incorporating into kits for PCR-based detection is contemplated to be a part of the present disclosure.

TABLE 15

| Sr. No. | List of components | Description |
| --- | --- | --- |
| 1. | One step RT-PCR mix (ORP) | PCR compatible buffer, dNTPs and DNA polymerase. Several custom formulations are available commercially |
| 2. | Reverse transcriptase (RT) | Several variants available commercially |
| 3. | ROX dye | Internal reference control dye available from several sources commercially |
| 4. | Nuclease free water | Available from several sources commercially |
| 5. | COVID-19 Assay 1 primer F (COVID-19-FP) | Any one of oligonucleotide primer pair as disclosed in the present disclosure. More primers can be used for performing multiplex PCR reactions. |
| 6. | COVID-19 Assay 1 primer R (COVID-19-RP) | Any one of oligonucleotide primer pair as disclosed in the present disclosure. More primers can be used for performing multiplex PCR reactions. |
| 7. | Random-hexamer primer | Available from several sources commercially |
| 8. | GAPDH primer F | Primer sequences obtained from literature, custom synthesized |
| 9. | GAPDH primer R | Primer sequences obtained from literature, custom synthesized |
| 10. | Positive control (in-vitro transcribed RNA) (PC) | Lab-synthesized RNA which contains the regions encompassing the biomarkers as well as human GAPDH mRNA as internal control |
| 11. | No-template control (NTC) | Nuclease-free water used as RNA-free negative control |
| 12. | Probe | Any one of the probe as disclosed in the present disclosure having compatibility with the oligonucleotide primer pair. |

Example 9

Use of the Biomarkers and the Oligonucleotide Primer Pairs as Disclosed in the Present Disclosure The Biomarkers as disclosed in the present disclosure have a vast potential for various applications. A nucleic acid fragment having a nucleic acid sequence with at least 95% identity to the nucleic acid sequence as set forth in any one of SEQ ID NO: 1 or 2 or 3 or 4 or 5 (biomarkers) can be used for developing vaccine against SARS-CoV-2. Such nucleic acid fragments can be used as epitopes to raise antibodies or make vaccines targeting SARS-CoV-2. The Biomarkers can be used for virus specific drug targeting. The oligonucleotide primers can be used to study variations arising in SARS-CoV-2 genome. Combinations of the different primers as disclosed herein can be used to sequence smaller or bigger regions of SARS-CoV-2 genome. A nucleic acid fragment having a nucleic acid sequence with at least 95% identity to the nucleic acid sequence as set forth in any one of SEQ ID NO: 1 or 2 or 3 or 4 or 5 (biomarkers) can be used to detect specific regions of the virus genome by hybridization. The region thus bound will emit fluorescence and can be detected.

Advantages of the Present Disclosure

The present disclosure discloses the biomarkers for detecting the presence of SARS-CoV-2 from a sample, and also for developing therapeutic interventions for the treatment of infections caused by SARS-CoV-2. The present disclosure discloses the oligonucleotide primer sets which can be used for detecting the presence of COVID-19 in a sample. The primary advantage of the present disclosure lies in the accurate detection of the presence of SARS-CoV-2. The primer sets as disclosed herein provides an early and specific detection of SARS-CoV-2 which is desirable for starting an early treatment regime for treating the infection. The kit as disclosed in the present disclosure comprises the components with which one can efficiently detect the presence of SARS-CoV-2 using either a probe-free PCR detection method or a probe-free PCR detection method.

Owing to the high specificity and sensitivity of the oligonucleotide primer pairs as disclosed herein, probe-free method can be applied which shows accuracy similar to the one shown with the probe-based method. Therefore, using the primer pairs as disclosed herein probe-free method can be applied at a commercially viable scale. Also, avoiding the use of specifically designed probes without leveraging the specificity of the reaction, the primer pair as disclosed herein also provides an economically viable option for detecting the presence of SARS-CoV-2 in a sample. Therefore, the biomarkers, primer sets, and the kit for detecting the presence of SARS-CoV-2 as disclosed herein would help in timely containment of the spread of the COVID-19 which could prevent loss of lives at large.

We claim:

1. A method of detecting the presence of an amplicon of a gene from severe acute respiratory syndrome coronavirus 2 (SARS-COV-2) in a sample, said method comprising:
   a) isolating RNA from a sample;
   b) preparing DNA from RNA by reverse transcriptase reaction;
   c) performing nucleic acid amplification reaction employing an oligonucleotide primer pair to produce an amplicon, wherein the set of primer pairs is selected from the group consisting of a nucleic acid sequence as set forth in SEQ ID NO: 6 and SEQ ID NO: 7, SEQ ID NO: 8 and SEQ ID NO: 9, SEQ ID NO: 6 and SEQ ID NO: 9, SEQ ID NO: 10 and SEQ ID NO: 11, SEQ ID NO: 12 and SEQ ID NO: 13, SEQ ID NO: 6 and SEQ ID NO: 13, SEQ ID NO: 6 and SEQ ID NO: 11, SEQ ID NO: 8 and SEQ ID NO: 11, SEQ ID NO: 8 and SEQ ID NO: 13, SEQ ID NO: 10 and SEQ ID NO: 13, and SEQ ID NO: 12 and SEQ ID NO: 11; and
   d) detecting the presence of the amplicon.

2. A method of detecting the presence of an amplicon of a gene from severe acute respiratory syndrome coronavirus 2 (SARS-COV-2) in a sample, said process comprising:
   a) preparing nucleic acid from a sample;
   b) performing nucleic acid amplification reaction employing the nucleic acid of step (a) and one or more oligonucleotide primer pairs for producing one or more amplicons, wherein the amplicon comprises a nucleic acid sequence selected from the group consisting of SEQ ID NO: 1, SEQ ID NO: 2, SEQ ID NO: 3, and SEQ ID NO: 4; and
   c) detecting the presence of one or more amplicons.

3. A method of detecting the presence of severe acute respiratory syndrome coronavirus 2 (SARS-COV-2) in a sample, said process comprising: a) isolating RNA from a sample; b) preparing DNA from RNA by reverse transcriptase reaction; c) performing nucleic acid amplification reaction employing an oligonucleotide primer pair for amplifying a fragment in the presence of a probe capable of binding to the fragment, wherein the oligonucleotide primer pair is selected from the group consisting of a nucleic acid sequence as set forth in SEQ ID NO: 6 and SEQ ID NO: 7, SEQ ID NO: 8 and SEQ ID NO: 9, SEQ ID NO: 10 and SEQ ID NO: 11, SEQ ID NO: 12 and SEQ ID NO: 13, and wherein the probe comprises a nucleic acid sequence as set forth in SEQ ID NO: 18 or SEQ ID NO: 20, or SEQ ID NO: 21, and a fluorophore and a quencher linked to the probe; and d) detecting whether SARS-COV-2 is present in the sample by the presence of the signal from the fluorophore.

4. The method of claim 1, wherein the sample is selected from the group consisting of sputum, blood, swab, lung biopsy, pleural fluid, and tracheal aspirate.

5. The method of claim 1, wherein detecting the presence or absence of the amplicon is done using a fluorescent dye.

6. The method of claim 5, wherein the fluorescent dye is selected from the group consisting of SYBR Green, EvaGreen, SYTO-13, SYTO-16, SYTO-80, SYTO-82, and BEBO.

7. The method of claim 3, wherein the fluorophore and the quencher is selected from the group consisting of FAM and BHQ0, FAM and BHQ1, HEX and BHQ1, CY5 and BHQ3, FAM and TAMRA, and TET and TAMRA.

8. The method of claim 2, wherein the oligonucleotide primer pair consisting of a first primer consisting of a nucleic acid sequence as set forth in SEQ ID NO: 6, and a second primer consisting of a nucleic acid sequence as set forth in SEQ ID NO: 7, is capable of producing the amplicon comprising a nucleic acid sequence as set forth in SEQ ID NO: 1 or SEQ ID NO: 2.

9. The method of claim 2, wherein the oligonucleotide primer pair consisting of a first primer consisting of a nucleic acid sequence as set forth in SEQ ID NO: 8, and a second primer consisting of a nucleic acid sequence as set forth in SEQ ID NO: 9, is capable of producing the amplicon comprising a nucleic acid sequence as set forth in SEQ ID NO: 3.

10. The method of claim 2, wherein the oligonucleotide primer pair consisting of a first primer consisting of a nucleic acid sequence as set forth in SEQ ID NO: 10, and a second primer consisting of a nucleic acid sequence as set forth in SEQ ID NO: 11, or a first primer having a nucleic acid sequence as set forth in SEQ ID NO: 12, and a second primer having a nucleic acid sequence as set forth in SEQ ID NO: 13, is capable of producing the amplicon comprising a nucleic acid sequence as set forth in SEQ ID NO: 4.

11. The method of claim 3, wherein the oligonucleotide primer pair consists of a nucleic acid sequence as set forth in SEQ ID NO: 6 and SEQ ID NO: 7, and wherein the probe consists of a nucleic acid sequence as set forth in SEQ ID NO: 20.

12. The method of claim 3, wherein the oligonucleotide primer pair consists of a nucleic acid sequence as set forth in SEQ ID NO: 8 and SEQ ID NO: 9, and wherein the probe comprises a nucleic acid sequence as set forth in SEQ ID NO: 21.

13. The method of claim 3, wherein the oligonucleotide primer pair consists of a nucleic acid sequence as set forth in SEQ ID NO: 10 and SEQ ID NO: 11, or SEQ ID NO: 12 and SEQ ID NO: 13, and wherein the probe comprises a nucleic acid sequence as set forth in SEQ ID NO: 18.

14. The method of claim 2, wherein preparing nucleic acid from the sample comprises: (a) isolating RNA from the sample; and (b) performing reverse transcriptase reaction to obtain DNA.

15. A probe having a fluorophore and a quencher linked to the probe, wherein the probe comprises a nucleic acid sequence of at least 20 nucleotides in length as set forth in any one of SEQ ID NO: 18, SEQ ID NO: 19, SEQ ID NO: 20, or SEQ ID NO: 21.

16. The probe as claimed in claim 15, wherein the probe comprises a nucleic acid sequence as set forth in SEQ ID NO: 18, or SEQ ID NO: 20, or SEQ ID NO: 21.

17. A kit comprising: (a) one or more oligonucleotide primers pair selected from the group consisting of a nucleic acid sequence as set forth in SEQ ID NO: 6 and SEQ ID NO: 7, SEQ ID NO: 8 and SEQ ID NO: 9, SEQ ID NO: 6 and SEQ ID NO: 9, SEQ ID NO: 10 and SEQ ID NO: 11, SEQ ID NO: 12 and SEQ ID NO: 13, SEQ ID NO: 6 and SEQ ID NO: 13, SEQ ID NO: 6 and SEQ ID NO: 11, SEQ ID NO: 8 and SEQ ID NO: 11, SEQ ID NO: 8 and SEQ ID NO: 13, SEQ ID NO: 10 and SEQ ID NO: 13, and SEQ ID NO: 12 and SEQ ID NO: 11; (b) a fluorescent dye; and (c) a buffer.

18. A kit comprising: (a) one or more oligonucleotide primer pairs selected from the group consisting of a nucleic acid sequence as set forth in SEQ ID NO: 6 and SEQ ID NO: 7, SEQ ID NO: 8 and SEQ ID NO: 9, SEQ ID NO: 6 and SEQ ID NO: 9, SEQ ID NO: 10 and SEQ ID NO: 11, SEQ ID NO: 12 and SEQ ID NO: 13, SEQ ID NO: 6 and SEQ ID NO: 13, SEQ ID NO: 6 and SEQ ID NO: 11, SEQ ID NO: 8 and SEQ ID NO: 11, SEQ ID NO: 8 and SEQ ID NO: 13, SEQ ID NO: 10 and SEQ ID NO: 13, and SEQ ID NO: 12 and SEQ ID NO: 11; (b) one or more probes of claim 15; and (c) a buffer.

* * * * *

SEQUENCE LISTING

```
<160> NUMBER OF SEQ ID NOS: 27

<210> SEQ ID NO 1
<211> LENGTH: 24
<212> TYPE: DNA
<213> ORGANISM: Artificial Sequence
<220> FEATURE:
<223> OTHER INFORMATION: depicts the nucleic acid sequence of Biomarker
      1

<400> SEQUENCE: 1
tctgggacca atggtactaa gagg                                          24

<210> SEQ ID NO 2
<211> LENGTH: 18
<212> TYPE: DNA
<213> ORGANISM: Artificial Sequence
<220> FEATURE:
<223> OTHER INFORMATION: depicts the nucleic acid sequence of Biomarker
      2

<400> SEQUENCE: 2
cacaaaaaca acaaaagt                                                 18

<210> SEQ ID NO 3
<211> LENGTH: 18
<212> TYPE: DNA
<213> ORGANISM: Artificial Sequence
<220> FEATURE:
<223> OTHER INFORMATION: depicts the nucleic acid sequence of Biomarker
      3

<400> SEQUENCE: 3
ggtgattctt cttcaggt                                                 18

<210> SEQ ID NO 4
<211> LENGTH: 24
<212> TYPE: DNA
<213> ORGANISM: Artificial Sequence
<220> FEATURE:
<223> OTHER INFORMATION: depicts the nucleic acid sequence of Biomarker
      4

<400> SEQUENCE: 4
cagactaatt ctcctcggcg ggca                                          24

<210> SEQ ID NO 5
<211> LENGTH: 63
<212> TYPE: DNA
<213> ORGANISM: Artificial Sequence
<220> FEATURE:
<223> OTHER INFORMATION: depicts the nucleic acid sequence of biomarker
      5

<400> SEQUENCE: 5
ttggtcaaca agacggcagt gaggacaatc agacaactac tattcaaaca attgttgagg   60
ttc                                                                 63

<210> SEQ ID NO 6
<211> LENGTH: 23
```

```
<212> TYPE: DNA
<213> ORGANISM: Artificial Sequence
<220> FEATURE:
<223> OTHER INFORMATION: depicts forward primer sequence of the primer
      set APAP 1

<400> SEQUENCE: 6
atacatgtct ctgggaccaa tgg                                            23

<210> SEQ ID NO 7
<211> LENGTH: 29
<212> TYPE: DNA
<213> ORGANISM: Artificial Sequence
<220> FEATURE:
<223> OTHER INFORMATION: depicts reverse primer sequence of the primer
      set APAP 1

<400> SEQUENCE: 7
acttttgttg tttttgtggt aataaacac                                      29

<210> SEQ ID NO 8
<211> LENGTH: 24
<212> TYPE: DNA
<213> ORGANISM: Artificial Sequence
<220> FEATURE:
<223> OTHER INFORMATION: depicts forward primer sequence of the primer
      set APAP 2

<400> SEQUENCE: 8
gactcctggt gattcttctt cagg                                           24

<210> SEQ ID NO 9
<211> LENGTH: 24
<212> TYPE: DNA
<213> ORGANISM: Artificial Sequence
<220> FEATURE:
<223> OTHER INFORMATION: depicts reverse primer sequence of the primer
      set APAP 2

<400> SEQUENCE: 9
acagtgaagg atttcaacgt acac                                           24

<210> SEQ ID NO 10
<211> LENGTH: 22
<212> TYPE: DNA
<213> ORGANISM: Artificial Sequence
<220> FEATURE:
<223> OTHER INFORMATION: depicts forward primer sequence of the primer
      set APAP 3

<400> SEQUENCE: 10
gactcagact aattctcctc gg                                             22

<210> SEQ ID NO 11
<211> LENGTH: 22
<212> TYPE: DNA
<213> ORGANISM: Artificial Sequence
<220> FEATURE:
<223> OTHER INFORMATION: depicts reverse primer sequence of the primer
      set APAP 3

<400> SEQUENCE: 11
gacactggta gaatttctgt gg                                             22

<210> SEQ ID NO 12
<211> LENGTH: 20
<212> TYPE: DNA
```

```
<213> ORGANISM: Artificial Sequence
<220> FEATURE:
<223> OTHER INFORMATION: depicts forward primer sequence of the primer
      set APAP 4

<400> SEQUENCE: 12
tcagactaat tctcctcggc                                              20

<210> SEQ ID NO 13
<211> LENGTH: 22
<212> TYPE: DNA
<213> ORGANISM: Artificial Sequence
<220> FEATURE:
<223> OTHER INFORMATION: depicts reverse primer sequence of the primer
      set APAP 4

<400> SEQUENCE: 13
atttgtgggt atggcaatag ag                                           22

<210> SEQ ID NO 14
<211> LENGTH: 20
<212> TYPE: DNA
<213> ORGANISM: Artificial Sequence
<220> FEATURE:
<223> OTHER INFORMATION: depicts forward primer sequence of the primer
      set APAP 5

<400> SEQUENCE: 14
cacttctgct gctcttcaac                                              20

<210> SEQ ID NO 15
<211> LENGTH: 20
<212> TYPE: DNA
<213> ORGANISM: Artificial Sequence
<220> FEATURE:
<223> OTHER INFORMATION: depicts reverse primer sequence of the primer
      set APAP 5

<400> SEQUENCE: 15
gcttcttcca caatgtctgc                                              20

<210> SEQ ID NO 16
<211> LENGTH: 19
<212> TYPE: DNA
<213> ORGANISM: Artificial Sequence
<220> FEATURE:
<223> OTHER INFORMATION: depicts forward primer sequence of the primer
      set APAP 6

<400> SEQUENCE: 16
cttctgctgc tcttcaacc                                               19

<210> SEQ ID NO 17
<211> LENGTH: 19
<212> TYPE: DNA
<213> ORGANISM: Artificial Sequence
<220> FEATURE:
<223> OTHER INFORMATION: depicts reverse primer sequence of the primer
      set APAP 6

<400> SEQUENCE: 17
tctgattgtc ctcactgcc                                               19

<210> SEQ ID NO 18
<211> LENGTH: 33
<212> TYPE: DNA
<213> ORGANISM: Artificial Sequence
```

```
<220> FEATURE:
<223> OTHER INFORMATION: depicts the probe for the oligonucleotide
      primer pairs APAP 3 and APAP 4

<400> SEQUENCE: 18
agtcaatcca tcattgccta cactatgtca ctt                                   33

<210> SEQ ID NO 19
<211> LENGTH: 30
<212> TYPE: DNA
<213> ORGANISM: Artificial Sequence
<220> FEATURE:
<223> OTHER INFORMATION: depicts the probe for the oligonucleotide
      primer pair APAP 5

<400> SEQUENCE: 19
acggcagtga ggacaatcag acaactacta                                       30

<210> SEQ ID NO 20
<211> LENGTH: 25
<212> TYPE: DNA
<213> ORGANISM: Artificial Sequence
<220> FEATURE:
<223> OTHER INFORMATION: depicts the probe for the oligonucleotide
      primer pair APAP 1

<400> SEQUENCE: 20
gaagtctaac ataataagag gctgg                                            25

<210> SEQ ID NO 21
<211> LENGTH: 25
<212> TYPE: DNA
<213> ORGANISM: Artificial Sequence
<220> FEATURE:
<223> OTHER INFORMATION: depicts the probe for the oligonucleotide
      primer pair APAP 2

<400> SEQUENCE: 21
agatgctgta gactgtgcac ttgac                                            25

<210> SEQ ID NO 22
<211> LENGTH: 252
<212> TYPE: DNA
<213> ORGANISM: Artificial Sequence
<220> FEATURE:
<223> OTHER INFORMATION: depicts the nucleic acid sequence of the
      amplicon as obtained by performing PCR using the oligonucleotide
      primer pair APAP 1

<400> SEQUENCE: 22
atacatgtct ctgggaccaa tggtactaag aggtttgata accctgtcct accatttaat      60
gatggtgttt attttgcttc cactgagaag tctaacataa taagaggctg gattttggt     120 actactttag attcgaagac ccagtcccta cttattgtta ataacgctac taatgttgtt    180
attaaagtct gtgaatttca attttgtaat gatccatttt tgggtgttta ttaccacaaa    240
aacaacaaaa gt                                                        252

<210> SEQ ID NO 23
<211> LENGTH: 177
<212> TYPE: DNA
<213> ORGANISM: Artificial Sequence
<220> FEATURE:
<223> OTHER INFORMATION: depicts the nucleic acid sequence of the
      amplicon as obtained by performing PCR using the oligonucleotide
      primer pair APAP 2
```

<400> SEQUENCE: 23
gactcctggt gattcttctt caggttggac agctggtgct gcagcttatt atgtgggtta    60
tcttcaacct aggactttc tattaaaata taatgaaaat ggaaccatta cagatgctgt    120
agactgtgca cttgaccctc tctcagaaac aaagtgtacg ttgaaatcct tcactgt    177

<210> SEQ ID NO 24
<211> LENGTH: 165
<212> TYPE: DNA
<213> ORGANISM: Artificial Sequence
<220> FEATURE:
<223> OTHER INFORMATION: depicts the nucleic acid sequence of the
      amplicon as obtained by performing PCR using the oligonucleotide
      primer pair APAP 3

<400> SEQUENCE: 24
gactcagact aattctcctc ggcgggcacg tagtgtagct agtcaatcca tcattgccta    60
cactatgtca cttggtgcag aaaattcagt tgcttactct aataactcta ttgccatacc    120
cacaaatttt actattagtg ttaccacaga aattctacca gtgtc    165

<210> SEQ ID NO 25
<211> LENGTH: 124
<212> TYPE: DNA
<213> ORGANISM: Artificial Sequence
<220> FEATURE:
<223> OTHER INFORMATION: depicts the nucleic acid sequence of the
      amplicon as obtained by performing PCR using the oligonucleotide
      primer pair APAP 4

<400> SEQUENCE: 25
tcagactaat tctcctcggc gggcacgtag tgtagctagt caatccatca ttgcctacac    60
tatgtcactt ggtgcagaaa attcagttgc ttactctaat aactctattg ccatacccac    120
aaat    124

<210> SEQ ID NO 26
<211> LENGTH: 255
<212> TYPE: DNA
<213> ORGANISM: Artificial Sequence
<220> FEATURE:
<223> OTHER INFORMATION: depicts the nucleic acid sequence of the
      amplicon as obtained by performing PCR using the oligonucleotide
      primer pair APAP 5

<400> SEQUENCE: 26
cacttctgct gctcttcaac ctgaagaaga gcaagaagaa gattggttag atgatgatag    60
tcaacaaact gttggtcaac aagacggcag tgaggacaat cagacaacta ctattcaaac    120
aattgttgag gttcaacctc aattagagat ggaacttaca ccagttgttc agactattga    180
agtgaatagt tttagtggtt atttaaaact tactgacaat gtatacatta aaaatgcaga    240
cattgtggaa gaagc    255

<210> SEQ ID NO 27
<211> LENGTH: 102
<212> TYPE: DNA
<213> ORGANISM: Artificial Sequence -continued

```
<220> FEATURE:
<223> OTHER INFORMATION: depicts the nucleic acid sequence of the
      amplicon as obtained by performing PCR using the oligonucleotide
      primer pair APAP 6

<400> SEQUENCE: 27
cttctgctgc tcttcaacct gaagaagagc aagaagaaga ttggttagat gatgatagtc      60
aacaaactgt tggtcaacaa gacggcagtg aggacaatca ga                        102
```